(12) United States Patent
Song et al.

(10) Patent No.: US 10,292,586 B2
(45) Date of Patent: May 21, 2019

(54) NON-INVASIVE HEALTH INDICATOR MONITORING SYSTEM AND USING METHOD THEREOF

(71) Applicant: KOREA INSTITUTE OF SCIENCE AND TECHNOLOGY, Seoul (KR)

(72) Inventors: Yong Won Song, Seoul (KR); Su Youn Lee, Seoul (KR); Ji Yeon Lee, Seoul (KR); Jung Ah Lim, Seoul (KR); Ji Won Choi, Seoul (KR); Byung Ki Cheong, Seoul (KR); Jin Seok Kim, Seoul (KR); Ho Seong Jang, Seoul (KR); Hyun Jung Yi, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 854 days.

(21) Appl. No.: 14/538,206

(22) Filed: Nov. 11, 2014

(65) Prior Publication Data

US 2015/0201837 A1 Jul. 23, 2015

(30) Foreign Application Priority Data

Jan. 20, 2014 (KR) ........................ 10-2014-0006857

(51) Int. Cl.
*A61B 5/00* (2006.01)
*A61B 5/145* (2006.01)
*A61B 5/1486* (2006.01)
*H01M 10/00* (2006.01)

(52) U.S. Cl.
CPC .......... *A61B 5/0002* (2013.01); *A61B 5/1486* (2013.01); *A61B 5/14507* (2013.01); *A61B 5/14532* (2013.01); *A61B 5/6821* (2013.01); *H01M 10/00* (2013.01); *A61B 2562/16* (2013.01)

(58) Field of Classification Search
CPC .............. A61B 2562/16; A61B 5/0002; A61B 5/14507; A61B 5/14532
See application file for complete search history.

(56) References Cited

U.S. PATENT DOCUMENTS

| 6,102,872 A * | 8/2000 | Doneen | A61B 5/14532 422/50 |
|---|---|---|---|
| 2014/0197802 A1* | 7/2014 | Yamazaki | H02J 7/0052 320/137 |

(Continued)

FOREIGN PATENT DOCUMENTS

| JP | 2005-502389 A | 1/2005 |
|---|---|---|
| JP | 2008-253635 A | 10/2008 |

OTHER PUBLICATIONS

Korean Office Action dated Feb. 17, 2015; Appln. No. 10-2014-0006857.

*Primary Examiner* — Patricia Mallari
*Assistant Examiner* — Michael A Catina
(74) *Attorney, Agent, or Firm* — Ladas & Parry LLP; Loren K. Thompson

(57) ABSTRACT

The present invention relates to a non-invasive health indicator monitoring system including a sensing module, an electric power storage module, and a circuit module to collect health indicator information by contacting with a subject. In addition, the present invention also relates to a method for monitoring health indicator continuously by using the health indicator monitoring system.

37 Claims, 17 Drawing Sheets

(56) References Cited

U.S. PATENT DOCUMENTS

| | | | | |
|---|---|---|---|---|
| 2014/0200424 A1* | 7/2014 | Etzkorn | ............... | A61B 5/1486 |
| | | | | 600/345 |
| 2014/0296674 A1* | 10/2014 | Etzkorn | ................ | G02C 7/083 |
| | | | | 600/345 |
| 2014/0338458 A1* | 11/2014 | Wang | ...................... | G01L 1/005 |
| | | | | 73/658 |
| 2015/0173680 A1* | 6/2015 | Etzkorn | .............. | A61B 5/6821 |
| | | | | 600/345 |

* cited by examiner

→ No apparent media toxicity

NON-INVASIVE HEALTH INDICATOR MONITORING SYSTEM AND USING METHOD THEREOF

BACKGROUND OF THE INVENTION

1. Field of the Invention

The present invention relates to a non-invasive health indicator monitoring system comprising a sensing module, a power storage module, and a circuit module to collect health indicator information by contacting with a subject.

In addition, the present invention further relates to a method for monitoring health indicator marker continuously by using the health indicator monitoring system.

2. Background of the Invention

In 2020, it is estimated that elderly population will reach about 16% of total population and market size of silver industry will be at least 10% of total industry in 2020. Meanwhile in the circumstances that the interest in health of old people and improvement of life quality become important according to increase of life expectancy, needs for developing cutting-edge converging technology contributable to treatment of senile chronic disease or complementation of damaged/deteriorated human body function are increasing.

Particularly for diseases like diabetes mellitus among the chronic diseases, by monitoring blood glucose level with self-monitoring method, risks for heart disease, renal damage, and blindness caused by diabetes can be reduced. Thus studies on glucose sensor have been globally active, and a number of articles have been published.

However, although about 30% of adults in Korea are classified as patients with diabetes/potential diabetes, existing diagnosis and monitoring for it has been based on the inefficient and painful invasive blood collection from human body, and there was no case of developing noninvasive monitoring system. Accordingly, a natural and continuous monitoring system, combined with more human friendly sensing technology, for chronic diseases like diabetes in daily life is urgently needed. In continuous monitoring of diabetes, fluctuation level of blood glucose as well as its mean level is important, because it is possible to obtain various information from that and provide accurate diagnosis and efficient treatment for condition of patients. Therefore, this continuous monitoring may be on the basis of customized medical service appropriate to each potential patient. However, the existing blood glucose measurements have lower reliability of measurement value because of larger deviation and some limits with only instant diagnosis of physician, methods to continuously monitor it for long term has been necessarily required. In addition, continuous monitoring can provide important information available in research and development of related new drug.

Accordingly, needs of noninvasive monitoring system for health or disease condition by integrating and materializing ultra-sensitive sensor, energy control element, and communication element through converging technology of NT, IT, BT and ET become more urgent and thus it is expected that it is possible to prepare future aging society actively and present solutions for it.

SUMMARY OF THE INVENTION

An object of the present invention is to provide a noninvasive health indicator monitoring system comprising a power generation module, a power storage module and a sensing module to collect health indicator information in contact with a subject.

Another object of the present invention is to provide a method for monitoring health indicator information continuously by using the health indicator monitoring system.

An aspect of the present invention to achieve the above objects is a noninvasive health indicator monitoring system comprising a sensing module to collect health indicator information obtained from at least one health indicator information; an power storage module located on a supporting substrate to provide power to the sensing module continuously; and a circuit module connected with the sensing module and the power storage module respectively to drive the sensing module, save or transmit the collected health indicator information, and control power supply of the system to collect at least one type of health indicator information in contact with a subject.

Another aspect of the present invention to achieve the above object is a method for noninvasively monitoring health indicator using a noninvasive health indicator monitoring system, comprising (i) collecting health indicator information obtained from at least one health indicator marker; and (ii) delivering the collected health indicator information continuously to external devices, wherein the noninvasive health indicator monitoring system collects at least one health indicator information in contact with a subject; and comprises (a) a sensing module to collect health indicator information obtained from at least one health indicator marker; (b) a power storage module located on a support board to provide electric power to the sensing module continuously; and (c) a circuit module connected with the sensing module and the power storage module respectively to drive the sensing module, save or transmit the collected health indicator information, and control power supply of the system.

The circuit module may comprise a sensor driving part to drive the sensing module, a data control part to control the health indicator information, a transmission part to deliver the health indicator information to external devices or all of them.

The system may further comprise a power generation module, and the power generation module may be connected with the power storage module to store the generated power in it.

The power generation module may comprise one selected from the group consisting of a thin film type solar cell part, a piezoelectric nanogenerator part, a triboelectric nanogenerator part, and the combinations thereof.

The thin film type solar cell part may comprise a quantum dot (QD), a photoelectric device, photon divisional nanoparticle or all of them. The quantum dot (QD) may comprise at least one selected from the group consisting of SnS, CuInSe, CuS, FeS and the combinations thereof.

The piezoelectric nanogenerator part may comprise a nano structure of lead-free piezoelectric nano wire comprising one selected from the group consisting of ZnO, NKN, BaTiO3 and the combinations thereof.

The triboelectric nanogenerator may comprise one nano structure selected from the group consisting of PDMS, polymeric nanostructure and the combinations thereof.

The sensing module may comprise a sensor part obtaining at least one health indicator information from at least one health indicator among chemical, electric, optical, thermal, and mechanical indicators.

The sensor part may comprise a multi-sensor array comprising at least two unit sensors.

The sensor part may comprise an enzymatic amperometric sensor, a non-enzymatic amperometric sensor or all of them.

The power storage module may comprise a laminated flexible thin film battery or a capacitor.

The laminated flexible thin film battery may comprise a grid structure having transparent or no more than 50 µm in width of micro lines.

The laminated flexible thin film battery may be a transparent laminated flexible thin film battery comprising transparent cathode material, transparent electrolyte, and transparent anode material.

The system comprises multilayer structure comprising the first, the second, and the third layer, wherein the first layer is in contact with the subject, the second layer is located on the first layer and comprises the power generation module and the circuit module, and the third layer is located on the second layer and comprises the sensing module.

The third layer may further comprise the power generation module.

The power generation module may comprise one selected from the group consisting of a quantum dot photoelectric device part, a piezoelectric nanogenerator part, a triboelectric nanogenerator part, and the combinations thereof.

The thin film type solar cell part may comprise a quantum dot (QD), a photoelectric device, photon divisional nanoparticle or all of them. The quantum dot (QD) may comprise one selected from the group consisting of SnS, CuInSe, CuS, FeS and the combinations thereof.

The piezoelectric nanogenerator part may comprise a nano structure of lead-free piezoelectric nano wire comprising one selected from the group consisting of ZnO, NKN, BaTiO3 and the combinations thereof.

The triboelectric nanogenerator part may comprise one nano structure selected from the group consisting of PDMS, polymeric nanostructure and the combinations thereof.

The multilayer structure may be at least partially transparent and generally flexible and have a shape of contact lens. In the system driving mode, the multilayer structure may be located between the eyeball and the eyelid.

The health indicator information is glucose level contained in blood and the health indicator may be glucose level in tear.

The health indicator may be one selected from the group consisting of glucose level, glycated albumin level, fructosamine level, 1,5-anhydroglucitol, uric acid level, lactic acid level, pyruvate level, ascorbate level, and the combinations thereof.

The sensing module, the power generation module, and the power storage module and the circuit module are connected together though interconnect and the interconnect may be biocompatible, flexible and transparent interconnect or micro interconnect with no more than 50 µm in width of line.

The interconnect may comprise one selected from the group consisting of conductive nanoparticle, nanosized metal structure, oxide semiconductor, conductive polymer, carbon nanotube, graphene and the combinations thereof.

The power storage module may comprise a laminated flexible thin film battery or a capacitor.

The laminated flexible thin film battery may comprise a grid structure having transparent or no more than 50 µm of micro line.

The laminated flexible thin film battery may be a transparent laminated flexible thin film battery comprising transparent cathode material, transparent electrolyte, and transparent anode material.

The sensing module may comprise a filter part to filter proteins and a sensor part to quantify the health indicator marker from a body fluid filtered through the filter part. The circuit module connected with the sensor part may obtain the health indicator information and save and transmit the obtained health indicator information.

The system may have a thickness of no more than 300 µm. On the center of the contact lens shaped multilayer structure, a light transmission part comprising micro interconnect which is transparent or has a thickness no more than eye resolution may be included. The light transmission part may have a diameter of 0.5~2 mm.

The sensor part may comprise an enzymatic amperometric sensor, a non-enzymatic amperometric sensor or all of them.

The enzymatic amperometric sensor may quantify glucose from enzymatic decomposition of glucose by glucose oxidase and the non-enzymatic amperometric sensor may quantify glucose by using electrocatalytic activity of the crystal face of metal nanoparticles involved in the sensor.

The sensor part may be a hybrid sensor comprising both the enzymatic amperometric sensor and the non-enzymatic amperometric sensor.

The metal nanoparticle may comprise one selected from the group consisting of Au, Pt and the combinations thereof.

The supporting substrate in the multilayer structure comprises a soft hydrogel material, the multilayer structure may further comprise a protective layer covering whole of the multilayer structure, and the protective layer may further comprise one selected from the group consisting of HEMA, soft hydrogel, silicone acrylate, and fluoro-silicone acrylate and the combinations thereof.

In the noninvasive health indicator monitoring system, the power storage module may be supplied with energy in wireless charging manner.

The wireless charging manner may be magnetic resonance.

DETAILED DESCRIPTION OF THE INVENTION

Figure 1A:
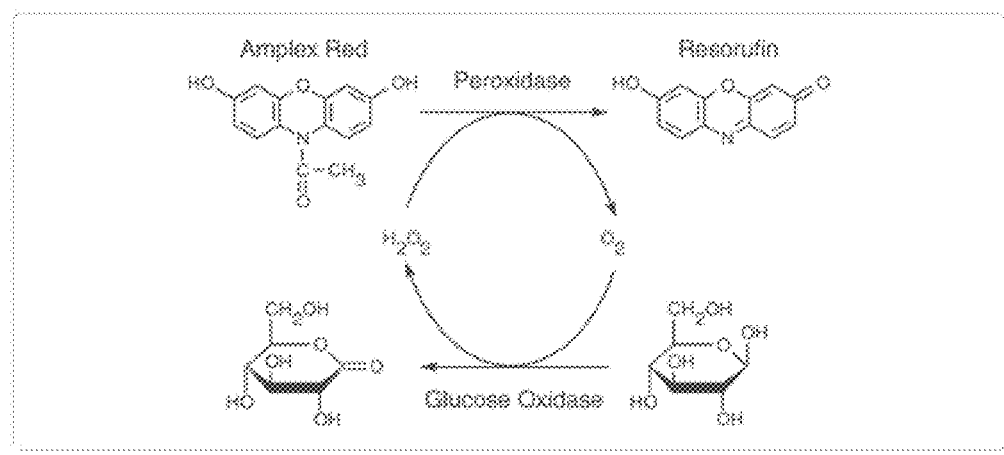
FIG. 1A shows a diagram of glucose level measuring mechanism using glucose oxidase.

Further scope of applicability of the present application will become more apparent from the detailed description given hereinafter.

An aspect of the present invention is a noninvasive health indicator monitoring system that comprises a power generation module located on the supporting substrate; a power storage module connected with the power generation module and storing electric power from the power generation module; and a sensing module to measure one health indicator marker and collects one type of health indicator information.

The present invention relates to painless, noninvasive, self-driving, body friendly/compatible type monitoring system that can monitor health indicator markers including disease condition continuously without invasion such as transplant/insertion, considering accessibility and convenience of the subject. Inventors of the present invention drew an optimal sensor device structure by developing a nano-bio-hybrid structure electrode to increase selectivity to marker and sensitivity of sensing. The system is self-driving without external power supply and continuous monitoring of health indicator markers possible by adapting energy producing (self nano power generation) and storing (battery) technology for human body contact type. Power is generated by combining solar cell and nanogenerator as self-power source for energy production and the generated power is stored in ultra-thin film type storing system. The energy produced and stored within the system can be used to communicate sensing signals and digital signals can be used as feedback format to the outside. This is not a passive system that depends on external energy source as necessary, but an active monitoring/feedback system that produces and uses energy within the system itself.

In general, health indicator information is difficult to identify accurate condition with only intermittent measurement of health indicator markers and even though average measurement values of the markers are similar, it is limited to provide accurate health condition due to different deviation. Accordingly, successional and continuous monitoring is required, and particularly for chronic diseases such as metabolic disease, the demand is further higher. The present invention is to provide a nano sensor capable of continuous monitoring with ultra-high sensitivity. The sensitivity and selectivity of the nano-sensor are improved dramatically by innovating its material surface treatment and its device structure.

In addition, the present invention may have a device unit to produce and store energy by itself without energy supply from the outside, as an active self-driving system. It is possible to drive the sensor continuously by generating and storing energy as necessary. The energy production is basically based on a photovoltaic device using solar energy and a nanogenerator using kinetic energy of the subject, and the generated energy is stored in high capacity flexible thin film type secondary battery having 3-D nano structure.

The present invention is a noninvasive system, which can be driven through either direct or indirect contact with the subject. To achieve such functions of the system, the flexible and transparent device fabrication and high device integration packaging technology for the system miniaturization are applied on the system. The system of the present invention may be a detachable monitoring system as necessary. Besides, the noninvasive system of the present invention may be a consumable.

In one example, the present invention may provide a system equipped with an external communication device as a continuous monitoring system. Thus, the system may comprise a circuit module further and the circuit module may be connected with the power storage module and the sensing module respectively to save or transmit the health indicator information and to control power supply of the system. The circuit module may comprise data storing part to save the health indicator information, a transmission part to transmit the health indicator to external devices, or all of them.

However, the monitoring system of the present invention does not necessarily need communication with the outside and can be materialized in a manner having self-recognition function. For example, the system of the present invention may be materialized in a manner to detect condition change of health indicator marker by visualization through contact display, alarm, and pain stimulus though electric shock without quantification.

In one example of the present invention, the sensing module may comprise a sensor part obtaining one health indicator information from at least one health indicator marker among chemical, electric, optical, thermal, and mechanical indicator markers.

The health indicator marker may be anything measurable and detectable through the sensor of the sensor part, including for example body fluid such as tear, saliva, urine, and sweat, substance level contained in body secretory substances including body odor, or vital signs such as body temperature and blood pressure, but is not limited in them.

The sensor should have sensitivity and selectivity to measure, detect, and quantify a targeted health indicator marker, and thus the nano electrode included in the sensor may comprise molecular wire that can approach a biochemical marker electrically, maintaining its electric property.

The sensor part may comprise an enzymatic amperometric sensor, a non-enzymatic amperometric sensor or all of them.

The amperometric sensor can measure, detect and quantify a health indicator marker through results of direct response to the marker, and it may be an enzymatic amperometric sensor using an enzyme or a non-enzymatic amperometric sensor sensing the marker directly without an enzyme. The enzymatic sensor has very excellent selectivity and the non-enzymatic sensor has a merit of superior stability because it directly treats the marker in electrochemical manner. The sensors can be used alone or in combination and when being equipped together, it is possible to compose an optimized noninvasive sensor system.

Especially, the enzymatic amperometric sensor can exchange electrons with a biochemical enzyme directly and efficiently by using the hybrid catalytic electrode employing the enzyme, catalyst, and low-dimensional material, and the selectivity and sensitivity of the sensor can be maximized by patterning the catalyst-enzyme hybrid electrode material customized with specific catalyst and mediator. Through the design and customized patterning of the electrode material, it is possible to elevate selectivity to the marker by controlling the system close to working potential of a specific marker. In the present invention, the enzymatic sensor may be a sensor based on the nano-bio hybrid material.

In another example, the noninvasive monitoring system may be a multilayer structure.

In a specific example, the multilayer structure may comprise the first, second, and third layer. The system comprises multilayer structures comprising the first, second, and third layer, wherein the first layer is located in contact with the subject to protect the subject, the second layer is located on the first layer and may comprise the power storage module and the circuit module, and the third layer is located on the second layer and may comprise the power generation module, the sensing module, and a membrane structure able to control flow of tear. The tear is coated on the outer surface of the third layer and the coated continuous tear is collected and used for sensing by the membrane structure. The collection is accomplished in state that there is no additional production of tear by stimuli.

In another specific example, the multilayer may be totally flexible, enough to have a shape of contact lens, and be transparent at least partially. In the system driving mode, the multilayer structure may be located between the eyeball and the eyelid.

When the noninvasive health indicator monitoring system is materialized in the shape of contact lens, the limited space of contact lens can be overcome by composing the above multilayer structure. The power generation module and the power storage module, which are the energy source, the sensing module comprising the sensor, and the circuit module with functions of information storage, analysis, and communication are integrated on the contact lens. In order to secure vision, the central optical zone within pupil dilation ranges should be transparent and some opaque devices may be located in peripheral fitting zones.

In a specific example, the multilayer structure may comprise the first, second, and third layer. Wherein the first layer is a part to be adhered to the eye and can be designed by using flexible hydrogel, considering the curve surface of eye. The first layer may be located in contact with a subject, the second layer may be located on the first layer and comprise modules difficult to be located on the first and the third layer, and the most outer layer, the third layer, may be located on the second layer and comprise the power generation module, the sensor module, and the membrane comprising a tear collector such as a pump and a pipe. In addition, the third layer is a part to collect tear, where a filter to filter macro protein as necessary may be located.

As the tear is coated and supplied from the outside of the third layer, the proactive membrane located on the third layer should have a tear collector and the nanogenerator module by kinetic energy of eyelid may be located on the third layer that can directly contact with the eyelid. In addition, the membrane comprising the tear collector can perform a function of protective membrane able to protect the first and the second layer.

The system may have a protective membrane structure comprising active or passive pumps, valves, and connecting pipes to supply tear to it, and this protective membrane can directly protect the sensor device. When the sensor device is exposed to the outside, there are some problems such that the sensor device may be damaged by motion and pressure of the eyelid and irritation feeling may occur by the exposed sensor device. Especially, the tear generated by the stimulus has significantly lower concentration of glucose content, a false detection by the sensor device may be problematic. Therefore, it is needed to isolate the sensor device from physical contact.

The protective membrane structure basically has a chamber where the tear can pool and a pipe structure to supply the tear to the chamber in the sensor device. Moreover, an additional device is needed to circulate fresh tear flow through the pipe continuously. An active or passive pump and valve are corresponding to this. The protective membrane structure may comprise a filter part, a component of the sensing module, to filter protein from the tear.

In a specific example, the active or passive pump may be made of flexible materials and be transparent. It is possible to circulate 0.5~1 μl per min of the secreted tear smoothly into the sensor device through the pipe. In each case of using or not using self-generated power in the system, the active or passive pump may be used. As the central part of the lens should be transparent optically, all the structures can be arranged within 5 mm of the lens perimeter.

The active pump has more than one chamber and actuator using electromagnetic force able to extrude the tear in the chamber by applying pressure to the chamber regularly. The size of chamber is about 2~3 mm in diameter and several tens of μm in height. Although the active pump may be made of same material with the system, it is possible to be substituted with a chip made of hard materials such as silicon or glass included in the protective structure.

The passive pump has at least one chamber, and a membrane structure on top of the chamber has a structure that the chamber can be pressed by pressure loaded on the surface of system. Pressure or motion of the eyelid can be used as a force able to press the chamber, resulting in extruding the tear from the chamber. As the eye blinks regularly at the level of 15~20 times per min, it is possible to use this motion as continuous external power source. The pressure of eyelid is known as 400 Pa in general and the top of chamber may have a prominent structure to deliver the pressure efficiently to the chamber. When the motion of the eyelid is used as compressed force of the chamber, a hoop shaped structure to deliver upward or downward motion of the eye lid can be added on the outside of protective membrane.

For the valve, a check valve and a diffuser valve may be used. The check valve has a structure that can be opened by pressure of fluid in only one direction and closed by pressure of fluid in the reverse direction. Check valves such as ring type, disk type, cantilever type and ball type can be used. The diffuser valve has a shape of pipe which is enlarged gradually in one direction and has a hydrodynamic character that the fluid flows well in the direction that the pipe is enlarged, but does not flow well in the reverse direction. A common shaped diffuser valve enlarged in 8~10° of angle may be used and have multi-step structure connected in series to obtain sufficient directivity.

The contact lens shaped system may be suitable for diagnosing and monitoring disease by measuring, detecting, and quantifying health indicator markers in the tear.

The tear has merits that it is possible to collect it continuously with noninvasive method and it is easy to collect it continuously through the fluid accumulated between the eye and the lens in wearing the contact lens. In addition, the tear is produced continuously at average 0.5~2.2 μl/min for human tear without special movement such as motion, so is a body fluid appropriate to measure, detect, and quantify biological substances, the markers of health indicator.

Most of the tear is composed of water and contains further minerals such as Na+, K+, Ca2+, and Mg2+, glucose, urea, lactate, pyruvate, and ascorbate. Since various chemical substances other than those can be contained in the tear according to development of disease, it is possible to diagnose the disease by analyzing them.

Thus in a specific example, the present invention provides a contact lens type system able to measure, detect, and quantify medical and biological substances in the tear, namely the health indicator markers, in noninvasive manner accurately and continuously by attaching it to the eye. The contact lens type system can be used for monitoring health or disease condition of a subject by obtaining health indicator information related to the health indicator markers from them in the tear.

Especially, the contact lens type system employs the glucose concentration as the health indicator marker. From the glucose level information in tear, the blood glucose level usually used as the information of diabetes diagnosis and continuous monitoring of diabetes is obtained. By correlating the glucose information in tear and blood, the contact lens type system can be used as the diabetes monitoring tool.

In other words, it is possible to substitute for traditional invasive blood glucose monitoring devices by measuring glucose level, a marker of diabetes, in the tear continuously. It is based upon the premise that there is a meaningful correlation between glucose level in blood and tear and thus in the present invention, correlation between levels of substance that may become a health indicator marker contained in the tear and the blood should be identified first. Especially, it is important to identify the correlation of glucose levels in the blood and the tear which become an indicator for diagnosis of diabetes.

It is possible to identify the correlation between glucose level in the tear and the blood by measuring them and comparing and analyzing their amount value statistically. When the Pearson's coefficient value obtained by substituting the average glucose level in the tear and the blood is more than 0.5, it is considered that there is correlation between the values. As the Pearson's coefficient between glucose level in the tear and the blood was 0.986, it was identified that they were correlated to each other. Therefore it is possible to diagnose and monitor diabetes by using glucose level in the tear as a maker of diabetes and in a specific example of the present invention, the system may be a noninvasive type diabetes monitoring contact lens.

In the present invention, the health indicator information is glucose level contained in blood and the health indicator marker may be glucose level in tear. In this case, the disease subject to diagnosis and monitoring may be diabetes.

In a specific example, the health indicator marker may be one selected from the group consisting of glucose level, glycated albumin level, fructosamine level, 1,5-anhydroglucitol, uric acid level, lactic acid level, pyruvate level, ascorbate level, and the combinations thereof.

Particularly in diagnosis and continuous monitoring of diabetes, the diagnosis and the monitoring is accomplished by measuring glucose level in patient's blood or tear, but accurate diagnosis and monitoring may be possible in combination with concurrent measurement of substance level associated with vascular complications comprising glycated albumin level, fructosamine level, and 1,5-anhydroglucitol level.

For example the glycated albumin, a changed form of normal albumin by glucose in body, may be a marker of diabetes representing glucose level indirectly as when blood glucose decreases, its amount is reduced further and on the contrary when blood glucose increases, the amount increases further.

In an example of the present invention, the sensing module included in the system of the present invention may comprise a filtering part to filter protein and a sensor part to quantify health indicator marker from body fluid filtered through the filtering part, and the circuit module connected with the sensor part may obtain the health indicator information and save and transmit the quantified health indicator information.

In an example of the present invention, the sensing module included in the system of the present invention may comprise an enzymatic amperometric sensor, a non-enzymatic amperometric sensor or all of them. Wherein, the enzymatic amperometric sensor may quantify glucose from decomposition of glucose by glucose oxidase and further quantify glucose by using both horseradish peroxidase (HRP) and glucose oxidase. The non-enzymatic amperometric sensor may quantify glucose by using electro catalytic activity according to crystal face or morphology of metal nanoparticle included in the sensor. Moreover, the sensor may be a hybrid type sensor to decompose glucose by using glucose oxidase and quantify the generated hydrogen peroxide by using metal particles.

The contact lens type diabetes monitoring system of the present invention is an enzymatic amperometric sensor and may comprise a glucose oxidase sensor. The principle of glucose oxidase sensor is as follows. When the glucose is decomposed into D-gluconolactone and hydrogen peroxide ($H_2O_2$), the current generated by oxidizing the produced hydrogen peroxide in electro-chemical methods will be read (Formula 1).

When quantifying the glucose by using HRP enzyme, the current reduced by HRP will be read (Formula 2).

$$H2O2 \rightarrow O2+2H++2e- \quad \text{(Formula 1)}$$

$$H2O2+2H++2e-(HRP) \rightarrow 2H2O \quad \text{(Formula 2)}$$

In case of the formula 2, precious metal nanoparticles may be used instead of HRP.

Figure 1B:
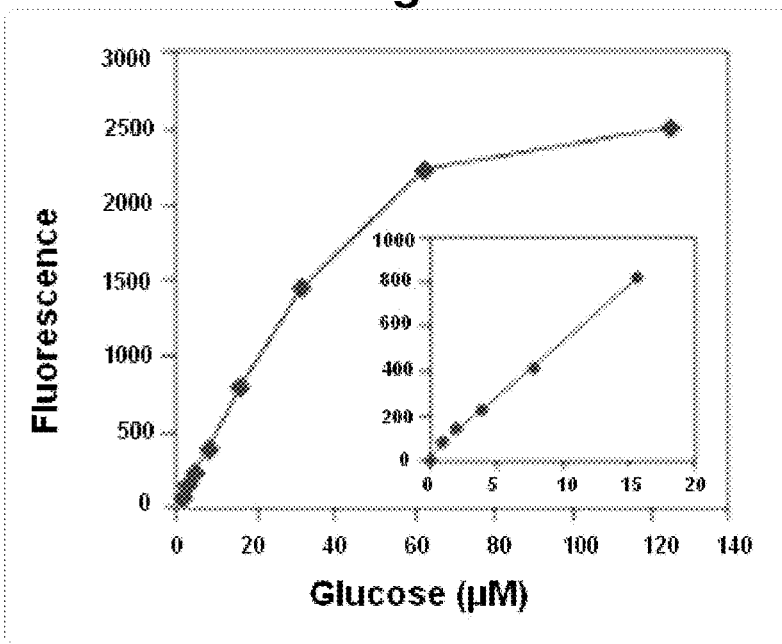
FIG. 1B shows fluorescence intensity spectrum for glucose level.
Figure 1C:
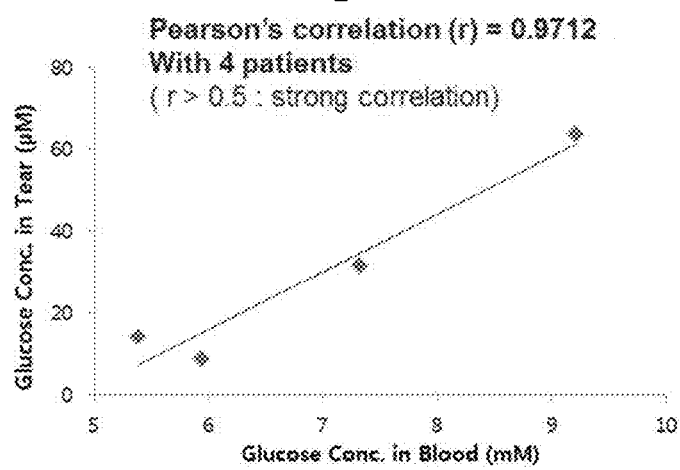
FIG. 1C shows correlation between glucose level in blood and glucose level in tear measured in 4 patients. There is strong correlation by more than 0.97 of Pearson index.

In case of quantifying glucose level with a general optical method, a red colored fluorescent material is produced by the reaction of Amplex®Red reagent and the hydrogen peroxide, which is generated by glucose oxidase. As results of the reaction, the produced red colored fluorescent material, called Resorufin, absorbs the light at 517 nm and emits the light at 585 nm. The reaction mechanism and fluorescent spectrum are illustrated in FIG. 1

The glucose oxidase sensor for monitoring of diabetes can monitor glucose amount accurately and quantitatively through current response to the glucose. The enzymatic sensor may be based on nano-bio hybrid material.

The non-enzymatic sensor may comprise precious metal nanoparticle sensor. Because the non-enzymatic sensor oxidizes glucose in electrochemical manner directly without dependence on enzyme, it has very excellent stability. The precious metal may have different electrocatalytic activity according to crystal faces and it is possible to prepare a nanoparticle sensor with improved selectivity. For example, when gold (Au) nanoparticle is spherical, the nanoparticle is synthesized by combining (100), (100) & (111), and (111) faces and exposing them to the surface and it is possible to select the most suitable appearance of nanoparticles for glucose oxidation. A branch type or low dimensional nanoparticle shape can improve selectivity and sensitivity through increase of surface area. When introducing Au—Pt binary metal nano crystals to the sensor, the electrocatalytic activity may be increased and its form may be alloy nano crystal, core/shell structure, and binary metal nano crystals such as Au-decorated Pt or Pt-decorated Au. Thus, the metal nanoparticle may comprise one selected from the group consisting of Au, Pt and the combinations thereof.

In an example of the present invention, the supporting substrate in the multilayer structure of the system may comprise soft hydrogel material and the multilayer structure may further comprise a protective membrane covering the whole of the multilayer structure. The protective membrane may be one selected from the group consisting of 2-hydroxy-ethylmethacrylate (HEMA), soft hydrogel, silicone acrylate, fluoro-silicone acrylate, and the combinations thereof.

To package each functional module included in the system of the present invention in the form of contact lens, a membrane with biocompatibility is needed. In case of soft contact lens used generally for human, its diameter is 13~14 mm and diameter of the central part where the pupil is located and that must be transparent is about 2 mm. As individual sensing module, power storage module, circuit module, and t power generation module as necessary should be integrated on a contact lens, the contact lens type system may be a multilayer-structured contact lens as mentioned previously. The thickness of contact lens for human may be about 300 μm at maximum and for example can comprise 3 layers. Each layer may have 10~100 μm of thickness, preferably 20~80 μm of thickness, more preferably 40~60 μm and the most preferably about 50 μm of thickness.

The first layer may be located in contact with a subject, the second layer may be located on the first layer and comprise modules difficult to be located on the first and the third layer, and the most outer layer, the third layer, may be located on the second layer and comprise the power generation module, the sensor module, and the membrane comprising a tear collector such as a pump and a tube.

The sensor module and the circuit module may be located on the edge of or on the whole lens excluding the position of pupil depending on the transparent degree, and for the power generation module may further be located on the edge of or on the whole lens excluding pupil.

As the tear is coated and supplied from the outside of the third layer, the proactive membrane located on the third layer should have a tear collector and the nanogenerator module by kinetic energy of eyelid may be located on the third layer that can contact with the eyelid directly. In addition, the membrane comprising the tear collector can perform a function of protective membrane able to protect the first and the second layer.

The contact lens type system is featured by stronger adhesiveness between layers and higher oxygen penetration ratio for driving sensor, using the multilayered membrane structure to integrate all the functional modules in the system in comparison with traditional multilayer contact lens.

Lenses for supporting substrate comprises soft hydrogel contact lens, hard contact lens (RGP) and hybrid contact lens. The hard lens may be easy to make each device contact each other and the soft hydrogel lens or the hybrid type contact has merits comprising larger surface area and smaller feeling of irritation when being attached with the eye of subject.

Oxygen permeability (OP) is an important consideration factor in selecting a contact lens. Especially, the diabetes marker monitoring contact lens of the present invention may use the enzymatic amperometric sensor using glucose oxidase wherein, as reduction of glucose using oxygen is an essential reaction, it is possible to control structure and materials of each layer to achieve oxygen penetration ratio within a range that the glucose sensor is operable, which is preferably at least ~50%.

For adhesion between membranes of each layer, a method to wrap upper and lower layer with 2-Hydroxy-Ethylmethacrylate (HEMA) may be used. The above method able to make at least 2 membranes each other is a sandwich manner and can make each layer adhered by connecting the membrane of each layer and then covering the upper and lower layer with HEMA in form of hydrogel. Through this, it is possible to make both the part contacting with the eye and the protective membrane adhered simultaneously and fix devices located on the inside of each layer without movement.

The connection of membrane on each layer may mean connection of functional modules located on each layer and may be accomplished with interconnect through printing or transferring.

In a specific example, the contact lens type system of the present invention may be a multilayer structure with no more than 300 μm of thickness. The system may comprise a light transmission part comprising micro interconnect having transparent or thickness no more than eye resolution on the center of the multilayer structure. The micro interconnect with thickness no more than eye resolution may be opaque. The light transmission part may have 0.5~2 mm of diameter.

In a specific example, the noninvasive health indicator monitoring system of the present invention may comprise a power generation module, a power storage module, and a sensing module, wherein the power generation module may comprise one selected from the group consisting of a thin film type solar cell part, a piezoelectric power generation part, a triboelectric nanogenerator part, and the combinations thereof.

The system of the present invention may produce electric power by itself, as an active self-driving system. For this, the system may comprise a photovoltaic device and a nanogenerator. They can be combined and equipped in a system and can achieve maximization and stabilization of power generation efficiency complementarily. The photovoltaic device may comprise a solar cell, and preferably is thin film type solar cell.

The thin film type solar cell may comprise QD (Quantum Dot) photovoltaic device, wherein the QDs may comprise one selected from the group SnS, CuInSe, CuS, FeS and the combinations thereof.

The QDs (Quantum dots), a nanoparticle of semiconductor, has a merit to control band gap energy continuously by controlling the size of particle. Since low priced process can be achieved by applying QDs to the solar cell, the product cost can be greatly reduced by applying the QDs compared to thin film type or mono-crystal semiconductor based solar cells. In applying the QDs to the solar cell, there may be 2 cases including substituting dye of dye sensitized solar cell with QDs and generating electron-hole pair on QD layer by applying colloidal QDs as an active layer. In early time, a hybrid type solar cell using both polymer and QD has been reported, but solar cells using only II-VI class as like PbS QD layer as an active layer has been reported gradually. However it is better to use a solar cell using Cd or Pb-free QD than Cd or Pb based QDs in terms of hazard or environment. Especially, in case of the solar cell used in the noninvasive health indicator monitoring system subject to living organisms, safety secured and eco-friendly materials are highly recommended as the solar cell materials. Therefore in the present invention, it is possible to synthesize Cd-free and Pb free QDs and apply them to the solar cell. Particularly, it is possible to materialize a solar cell achieving improvement of electrical continuity and improvement of optical absorption by synthesizing and then applying colloidal QDs such as SnS and CuInSe which have the environmental friendly composition, materializing close-packed assembly, and applying inorganic ligands.

In a specific example, the noninvasive health indicator system may comprise piezoelectric type or triboelectric nanogenerator. The power generation module device included in the system of the present invention may comprise a piezoelectric nanogenerator using Pb free piezoelectric nanowire such as ZnO or NKN or a nanogenerator to generate electric power by friction using PDMS or polymeric nanostructure, but is not limited in these. Therefore, the piezoelectric nanogenerator part may comprise one nano structure selected from the group consisting of Pb free piezoelectric nanowire such as ZnO, NKN, or BaTiO3.

The triboelectric nanogenerator part may comprise one nano structure selected from the group consisting of PDMS, polymeric nanostructure and the combinations thereof. The power of nano power generation is based on motion of subject, which for example may be originated from motion of eyelid, friction between part parts and pressure loaded on the system device.

In a specific example, the noninvasive health indicator monitoring system of the present invention may be a contact lens type system, wherein the power generation module included in the contact lens type system may comprise one selected from the group consisting of quantum dot photoelectric device part, a piezoelectric nanogenerator part, a triboelectric nanogenerator part, and the combinations thereof, the power generation module may be connected with the power storage module and wiring, and the interconnect may be transparent or micro wiring.

As the quantum dot photoelectric device part of the contact lens type system, namely photovoltaic part, may have insufficient amount of photon due to narrow area, it is needed to double the number of photons. For this, it is possible to use quantum cutting mechanism and accordingly improve the optical efficiency. For example, as described below a UV photon may be converted 2 visible ray photon through quantum partition.

1 UV photon→2 Visible Ray photon

For example when the power of light introduced into 1 $cm^2$ in an office with 500 lux of light intensity is about 0.7 mW and efficiency of solar cell included in 1 $cm^2$ is 1%, generated power is as follows.

$$0.7\ mW/cm^2 \times 0.01 = 0.007\ mW/cm2 = 7\ \mu W/cm^2$$

Consequently, in using a solar cell with about 1% of efficiency, it is possible to generate power in μW level and when the efficiency of solar energy is 0.1~0.5%, it is possible to generate power in similar level to the nanogenerator as 0.7~3.5 $\mu W/cm^2$. The efficiency of Cd free and Pb free QD solar cell is 0.05%, preferably 0.5% and it is possible to generate power sufficient to act as a self-driving system.

Other than photovoltaic part, the contact lens type system of the present invention can produce power with motion of eyelid by materializing piezoelectric nano structure or triboelectric nano structure. Subject to human body, energy obtainable from blink of eye is calculated as follows.

Average number of human blink: 15~20 times/min
Voltage output: 2 V
Current density: 8.13 $\mu A/cm^2$,
Power density: ~16 $\mu W/cm^2$
Maximum power obtainable from blink of eye: ~16.1 μW/blink (supposing diameter of contact lens as 0.7~0.9 cm).

As mentioned above, the nano structure may be Pb-free piezoelectric nano wire such as ZnO or NKN. The nanostructure may be made of PDMS or electrostatic nano polymer.

In a specific example, the noninvasive health indicator monitoring system of the present invention comprises a power generation module, a power storage module and a sensing module, wherein the power storage module may comprise a laminated flexible thin film battery or a capacitor. The laminated flexible thin film battery may comprise a grid structure having transparent or 20~200 µm of micro line width, preferably no more than 50 µm.

Currently, the secondary battery is usually used as a power source of mobile electronic information devices and this power source market of mobile electronic apparatuses has been highly maturated centering on lithium ion battery. Development of lithium battery has been expanded and developed to 1~several mW grade ultra-small/thin film type battery area to apply it in new ultra-small electronic apparatuses such as RFID, USN, smart care, and ultra-small health care system as well as medium and large battery area requiring several tens of KW of power. When comparing their performance in simply quantitative value aspect, the ubiquitous support ultra-small/thin film power storing device shows very low performance value property in comparison with the medium-large power source system. However, when converting it to concept of density, it may have 1.5~2 times higher performance value than that of medium-large battery.

In the present invention, the device that can be used as power source in the system is ultra-small thin film battery and may be transparent thin film battery as necessary. The thin film type battery used in the present invention may be a thin film type secondary battery, which is transparent and has high transmittance as necessary as a power source to store the generated power and provide it in driving and communication of sensor. The transparent and thin-film type secondary battery is a crucial component for materializing transparent display in the contact lens type system.

It is possible to use $LiCoO_2$, $LiNiO_2$, $LiMn_2O_4$, and $Li(NiCoMn)O_2$ as cathode materials of the thin film type secondary battery and olivine based $LiMPO_4$ cathode thin film having large band gap energy and high stability is also available to materialize a transparent battery. Although both liquid and solid electrolytes can be used for electrolyte of battery, it is better to use solid electrolyte with lower hazardous risks considering characteristics of the system.

In the present invention, the thin film battery may be a flexible transparent thin film battery. The transparency can be accomplished by using electrode structure with line width no more than resolution capacity of the eye in a form of mesh type, namely a grid form, or using transparent oxide or transparent Chalcogenide electrode. Even though the electrode active material, key material of the battery, is not transparent, a transparent battery can be achieved by composing a mesh type battery with no more than 50 µm of micro lines since maximum resolution capacity of human eyes is 50 µm. Or it is possible to materialize a transparent thin film type battery with nano thickness by using oxide active ingredient with wide band gap, for example olivine based materials. It is possible to obtain all solid state transparent thin film battery by using a substrate material with biocompatibility and applying transparent solid electrolyte and anode material, When materializing low temperature sintered electrode by using IPL (Intense Pulse Light) or KrF excimer laser, it is possible to make flexible transparent thin film battery with high energy density. When applying nano scale of thickness here, it is possible to obtain a thin film battery with lower energy loss due to excellent lithium migration degree.

In a specific example, the noninvasive health indicator monitoring system of the present invention may be the contact lens type system, wherein the power storage module included in the contact lens type system may comprise a laminated flexible thin film battery. The laminated flexible thin film battery may be a transparent laminated flexible thin film battery in a grid structure having micro line width.

The flexible/transparent secondary battery suitable to the contact lens type system of the present invention, namely the laminated flexible thin film battery, can prepare the cathode in a nano structure and be combined with Chalcogenide, a solid electrolyte, to secure transparency and flexibility. Thus, the flexible thin film battery may be transparent electrode/nano structure, cathode/chalcogenide/anode structure, graphene electrode/nano structure, cathode/chalcogenide/anode and graphene electrode/nano structure cathode/nano structure chalcogenide/anode. The chalcogenide solid electrolyte may have high ion conductance and high light penetration further.

In an example, the power storage module may receive energy in wireless manner. The wireless energy transmission is achieved by a method to use radiation, a method to use electromagnetic induction, and a non-radiation manner using short distance resonance phenomenon as a recently highlighted wireless energy delivery manner. In case a portable device, which is not provided with power through wire as like the non-invasive health indicator monitoring system of the present invention, it is required to generate electric power by itself or use an energy stored battery. Most home appliances, mobile equipment, office or industrial equipment use electric energy supplied through a wire from the power generator and store the electric power in a manner of recharging the energy to the battery through a wire. However, in case of battery having limited charging capacity, a recharge cycle becomes faster due to function improvement or multiple functions of the system and when increasing the charging capacity to complement this issue, there is a demerit that miniaturization becomes impossible. In addition, when not comprising a power generating system capable of self-power generation or consuming all of the energy in the battery in the circumstances that power generation is impossible, even though the system comprises the power generating module inside, a charging problem still appears. Thus, a system device requires wireless energy transmission and wireless charging matter. Especially, In case of a system that is able to contact with human body directly and indirectly similar to the present invention, it is required not only to secure safety and harmlessness to human body, but also to receive energy in a wireless manner.

Thus, in the present invention, a method to supply energy to the power storage module by using a magnetic resonance manner among wireless energy transmissions is selected.

Magnetic induction manner and electromagnetic wave manner have long been used. The magnetic induction manner has a merit of very high power transmission efficiency, at least 90%. However, it is a problem that the efficiency is dramatically lowered as low as only little power is transmitted when being off more than several cm or when the centers of transmission coil and reception coil does not coincide exactly. The electromagnetic wave manner can transmit higher power, at least several tens of kW to sites distant more than several tens km, but its efficiency is very low because considerable amount of the power is scattered and lost during the transmission process and it is critically harmful to human body. These are necessarily developed problems due to the nature of electromagnetic wave manner to radiate energy in the air by using both electric and magnetic field. To meet regulation on electromagnetic wave of each country, about 1 W of power transmission is limit.

A method that overcame limits of the traditional methods is magnetic resonance (or resonant magnetic coupling), which has short transmission distance and overcomes problems such as efficiency and human body harmfulness of the electromagnetic wave manner. The principle of resonant magnetic coupling is to generate magnetic field resonating with resonant frequency and transmit energy intensively only to the receiving part coil designed with same resonant frequency and has a merit capable of power transmission with very high efficiency up to several meter of transmission distance due to the nature of resonant magnetic coupling. Because the energy not absorbed into the reception part coil is not dissipated to the air in the form of radiation, but reabsorbed into the transmission part coil, the efficiency is higher; it is possible to transmit energy without any problem even though there is an obstacle like wall between the transmission part and the reception part; and it is very safe further because the energy is transmitted by using only magnetic field rarely absorbed in to the human body. The most important issue in the resonant magnetic coupling manner is to increase transmission distance and efficiency. When the frequency band where the transmitter-receiver induces resonance is smaller, it is possible to transmit power farther and with higher efficiency and it is required to maintain the quality factor (Q factor) very high for this. In the present invention, the quality factor was maintained high through appropriate use of nano technology and material technology and by controlling the circuit or frequency automatically by detecting changes of location and position of receiver and operational change through appropriate use of sensor and control technology. In addition it satisfies both regulations on electromagnetic interference (EMC) of each country and safety to human body (EMF) in power transmission at the level of several tens W by using frequency in several tens~several MHz of range with relatively lower absorption rate.

In an example, the noninvasive health indicator monitoring system of the present invention may select a manner to charge multiple system devices with a charger concomitantly.

The noninvasive health indicator monitoring self-driving system of the present invention needs interconnect as a mean to connect each functional module or as a lead frame of sensor module.

In an example, the interconnect included in the system may comprise one selected from the group consisting of flexibility and transparency secured graphene, carbon nanotube, transparent metal oxide, conductive polymer, metal nanostructure, metal oxide nanostructure and the combinations thereof.

The interconnect may be transparent interconnect or micro interconnect with no more than 50 μm of line width considering eye resolution.

In a specific example, the contact lens type system needs interconnect as a mean to connect each functional module or as a lead frame of sensor module further.

Especially, for a system attached to human body as like this contact lens type system, the interconnect should be biocompatible material also. Considering polymeric material of the lens, interconnect process should be possible at low temperature and the material should have excellent conductivity. In the present invention, interconnect for contact lens different from traditional interconnects that has been used for preparing traditional planar circuits is provided. The interconnect may be materialized in a manner of nano ink printing or graphene transfer using conductive nanoparticles, carbon nanotube, and graphene.

In order to connect each module in the contact lens type system, interconnect suitable to curved substrate and soft materials rather than a method by semiconductor process is needed. Because a contact lens is based on polymeric substrate, the interconnect of the present invention may be a high conductive, biocompatible nano ink capable of low temperature process on the polymeric substrate and the ink may be materialized into interconnect in a manner of printing. The material of nano ink may be metal nanoparticle, conductive polymer, and nano carbon, but is not limited in these. When materializing the interconnect with inkjet, it is better to print it to have a line width no more than eye resolution (~50 μm).

In addition, it is possible materialize a battery module, a power generator device module, and an interconnect for connecting between driving/communication circuit module by graphene transfer. The graphene interconnect may be a graphene interconnect that electrical conductivity is secured and separation from the synthesized substrate is easy for facilitating transfer just like the graphene used in the sensor. When using synthesis process and substrate surface properties, it is possible to control graphene grain size and provide graphene with easy attachment and separation. Beside as mentioned above, graphene may be used for a collector of sensor or a medium support as well as interconnect.

In a specific example, the interconnect included in the contact lens type system of the present invention may be transparent or micro interconnect with no more than 10 μm of line width and the interconnect may be arranged as a transparent of micro connect with thickness no more than eye resolution in the center of contact lens shape which may be a multilayer structure as necessary. The central region may be a light penetration part where light can penetrate and a region where the lens contact with the pupil or its dilatation region and have 0.5~2 mm of diameter.

Another aspect of the present invention is a method for monitoring health indicator to continuously obtain, save and transmit quantitative information for glucose level from tear by using the noninvasive health indicator monitoring system.

Effects of Invention

The self-driving, noninvasive health indicator monitoring system is a human body's side effect-free monitoring technology, which can not only collect basic information for improvement of individual health and life quality, but also innovate existing paradigm of feedback in monitoring system to replace the existing market. It is possible to reduce errors from transient measurement or test significantly through continuous monitoring of disease markers and play a significant role in development of new drug by enabling long term follow-up for drug efficacy. In addition, when it is materialized as a multi sensor array system capable of simultaneous monitoring for several disease markers, it may be possible to perform integrated sensing for various chemical/electrical/optical/thermal/mechanical phenomena related to health indicator and have higher sensitivity and selectivity due to mutual calibration between sensors. The system of the present invention is expected to be expandable as an ultimate portable display by convergence with transparent material/device and will be able to evolve toward a form able to embed contents.

EXAMPLE

Further scope of applicability of the present application will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from the detailed description.

<Example 1> Correlation Test Between Blood and Tear Glucose Level

For blood glucose level, blood glucose was estimated with a blood glucose self-monitoring device and plasma was obtained from collected venous blood and stored at −70° C. After collecting 10 μl of lachrymal solution from the eye of a patient using a micropipette with assistance of an eye doctor, the sample was put into a micro tube and stored at −70° C. Glucose level in the tear was measured with a fluorescent kit several times after diluting it to various concentrations. The measurement method was explained in the above, presented in FIG. 1. The correlation between the measured glucose in blood and tear was analyzed statistically and shown in FIG. 1(c). As shown in the results, it showed high correlation as over 0.97 of Pearson's coefficient.

<Example 2> Preparation of an Amperometric Enzyme Electrode and its Sensing Method In order to combine high selectivity of an enzyme and amperometric sensing method, a method to effectively hybridize carbon nanotubes having excellent electrical conductivity with enzymes is important. Thus in this example, a specific bio substance, M13 virus, having strong affinity to graphitic surface for hybridization between carbon nanotube and an enzyme, was used and an enzyme was chemically combined with the virus to prepare hybrid electrode.

Figure 2A:
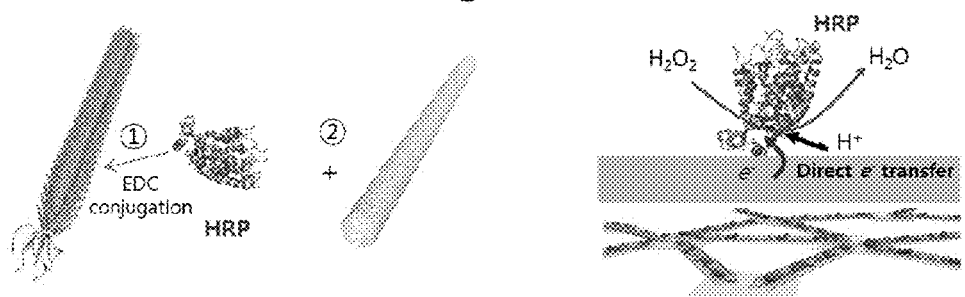
FIG. 2A shows a concept of specific virus and carbon nano pipe mixed electrode made by combination of specific virus and hydrogen peroxide reductase (HRP) and a hydrogen peroxide sensing mechanism using it.
Figure 2B:
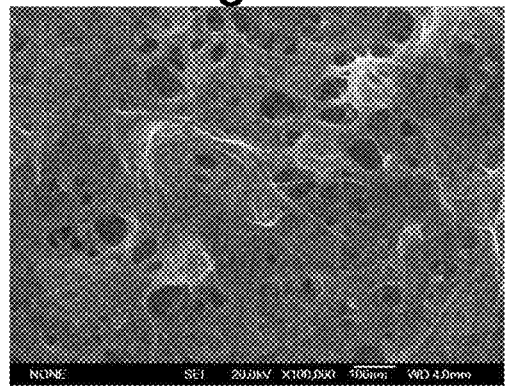
FIG. 2B shows a SEM (Scanning Electron Microscopy) image of a prepared mixed electrode sample.

Concretely, —COOH functional groups of HRP (Peroxidase type VI from horseradish) were activated to react with —$NH_2$ groups of other protein using 1-ethyl1-3-(3-dimethylaminopropyl) carboimide, HCl (EDC), N-hydroxysulfosuccinimide (sulfo-NHS) and then the enzyme was reacted and combined with the surface of protein of M13 virus which is specifically bound to carbon nanotube (FIG. 2(a)). After precipitating the enzyme bound M13 virus with polyethylene glycol 8000-NaCl solution (20 w/v %), it was purified with centrifuge and the purified enzyme-M13 virus was mixed with carbon nanotube dispersed in aqueous surfactant solution in 2:4 molar ratio (M13:SWNT=2:4 molar ratio) to prepare an electrode (FIG. 2(b)).

Figure 2C:
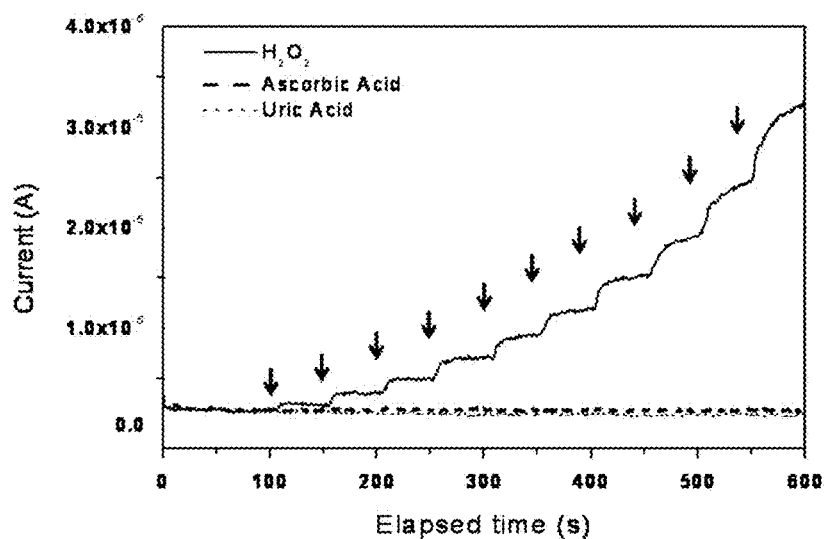
FIG. 2C represents amount of current produced by the prepared enzymatic electrode and ultra-high selectivity of the electrode for concentration change of H2O2, when using the electrode for materializing the enzymatic amperometric sensor.

To detect peroxide in amperometric manner using the hybrid electrode, a measurement was performed in PBS (phosphate-buffered solution, 100 mM phosphate, pH=7.4) by using carbon nanotube-enzyme electrode mounted on Au surface as a working electrode, Pt wire as a counter electrode, and Ag/AgCl (KCl saturated) as a reference electrode. The measurement voltage was fixed at −200 mV, and the current change was measured by adding 0.5 mM of target materials with 50 sec of interval. As shown in FIG. 2(c), it was found that the HRP combined hybrid electrode responded to only peroxide and did not respond to ascorbic acid and uric acid known widely as interfering factors in amperometric manner. In this amperometric measurement, it was possible to measure peroxide efficiently without any mediator generally used to increase efficiency of electron exchange between enzyme and electrode. Therefore in this example, it was identified apparently that the hybrid enzymatic electrode using M13 virus, carbon nanotube and enzyme had ultra-high selectivity and could be applied as high performance amperometric biosensor electrode due to direct electron exchange between the enzyme and the nano electrode, like carbon nanotube.

Figure 3:
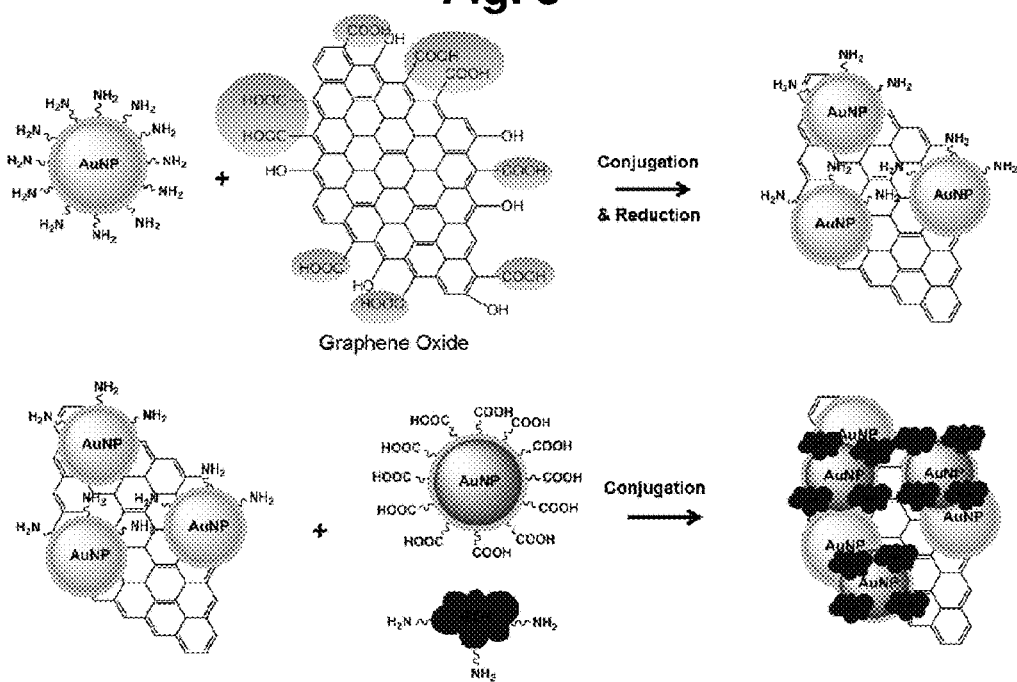
FIG. 3 shows a preparation principle of enzymatic amperometric type sensor material using gold nanoparticle and reduced graphene oxide schematically.

<Example 3> Development of an Amperometric Enzyme Sensor Using Gold Nanoparticle and Reduced Graphene Oxide For an amperometric enzyme (glucose oxidase) sensor, a nano-bio hybrid material was prepared using gold nanoparticle and reduced graphene oxide (rGO) known well as sensor materials. Carboxylic groups of the graphene oxide and amine functional groups of the gold nanoparticle were combined and then reduced by hydrazine to prepare gold nanoparticle-reduced graphene oxide hybrid material. EDC chemistry was applied to combine the nanoparticle-reduced graphene oxide material with glucose oxidase, and to attach amine-functionalized gold nanoparticles to carboxylic groups of other gold nanoparticles to increase the binding sites for the glucose oxidase as well as surface area. Brief experimental method was presented in FIG. 3. The developed sensor material was tested using SPE (screening printed electrode) and would be used in graphene based electrode later.

<Example 4> Preparation of the Precious Metal Nanoparticle with Gold/Platinum Core/Shell Structure Mix 3 ml of 20 mM $HAuCl_4$ solution with 3 ml of 20 mM $H2PtC_{l6}$, and then add 0.06 g of Pluronic F127 polymer in the mixture. After sonication of the mixture at room temperature for 15 min, add 6 ml of 0.1 M ascorbic acid solution. For homogeneous mixing, mix the reaction mixture with magnetic stir for 24 hr. During mixing for 24 hr, metal ion was reduced to form nano crystal particles with gold/platinum core/shell structure and the formed nanoparticles with core/shell structure was washed with acetone and dispersed and stored in DI water.

Figure 4A:
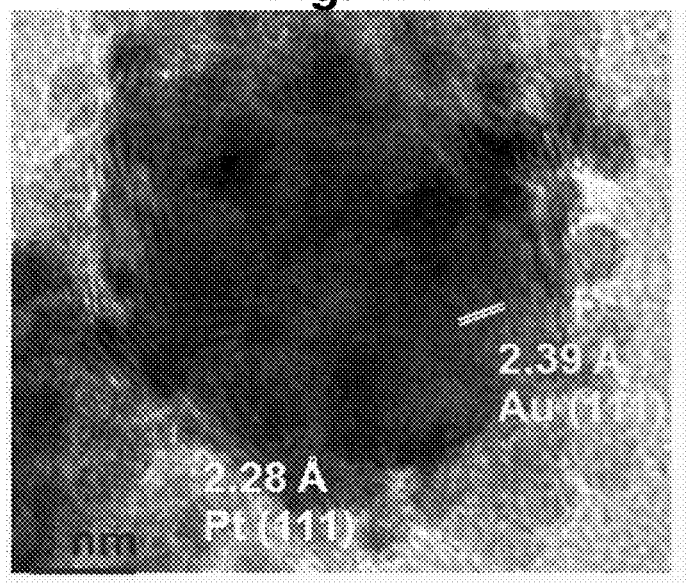
FIG. 4A shows a TEM (Transmission Electron Microscopy) image showing a core/shell nanostructure of gold (Au) and platinum (Pt) in materializing the non-enzymatic amperometric sensor.

FIG. 4(a) shows a TEM image of the prepared gold/platinum core/shell structure. Through lattice spacing of the measured nanoparticles, it was identified that large gold nanoparticles were formed in the core region and island shaped small platinum nanoparticles were formed on the gold nanoparticles.

Figure 4B:
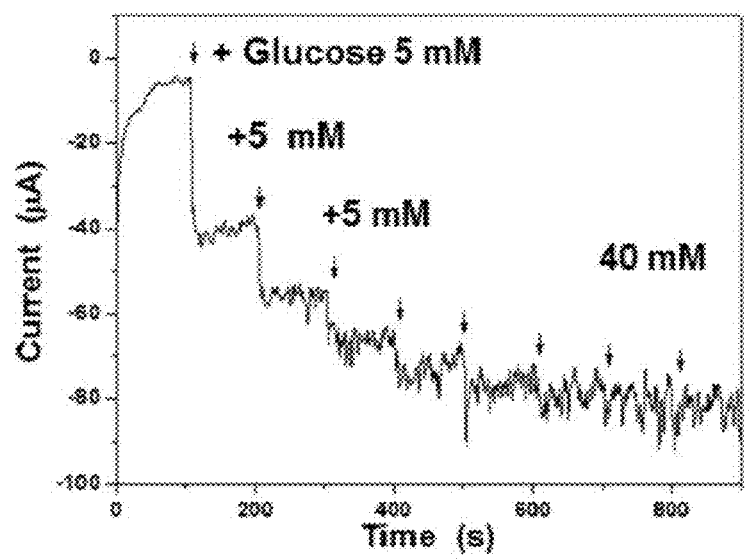
FIG. 4B shows current amount produced depending on glucose level in using the electrode based on the nanostructure.
Figure 5:
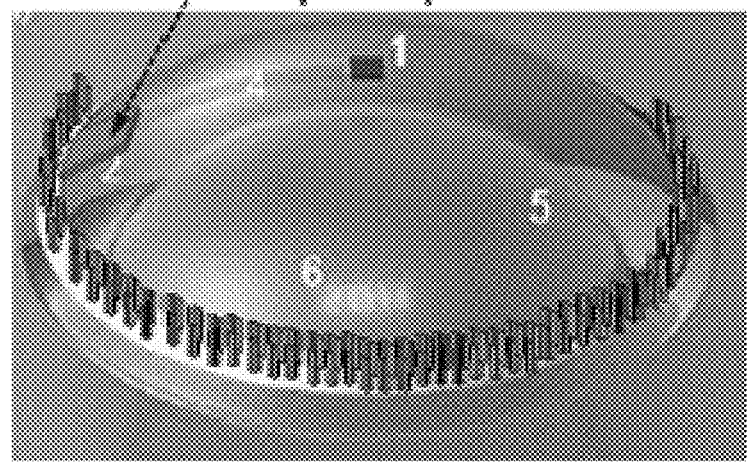
FIG. 5 is a diagram showing nanogenerator device equipped with the nano structure.
Figure 6A:
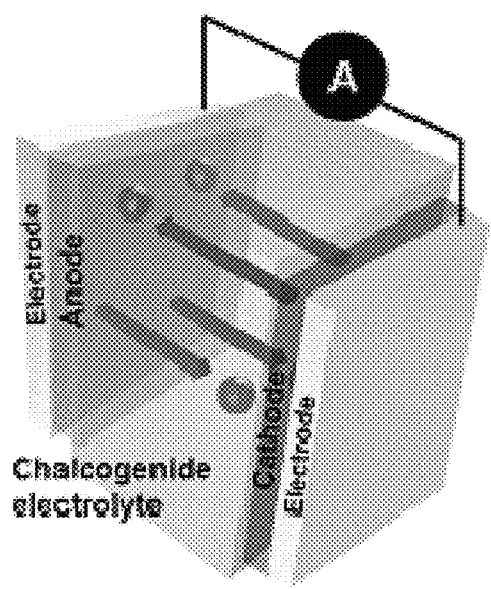
FIG. 6A shows a general solid electrolyte lithium ion secondary battery.
Figure 6B:
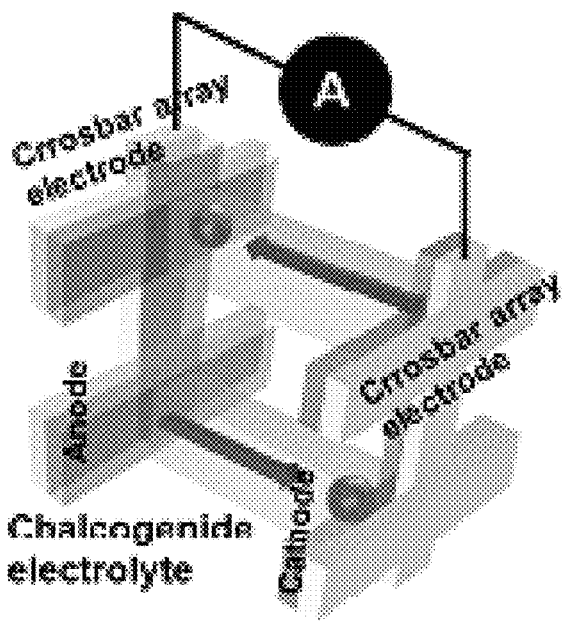
FIG. 6B shows a grid type transparent lithium ion secondary battery.
Figure 6C:
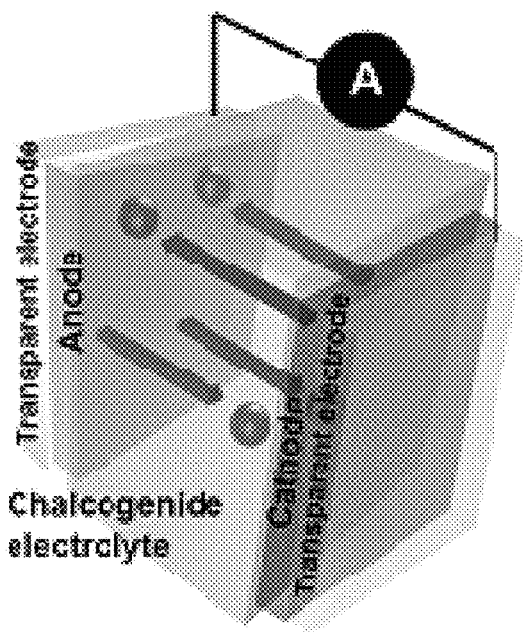
FIG. 6C shows a transparent electrode lithium ion secondary battery.
Figure 7:
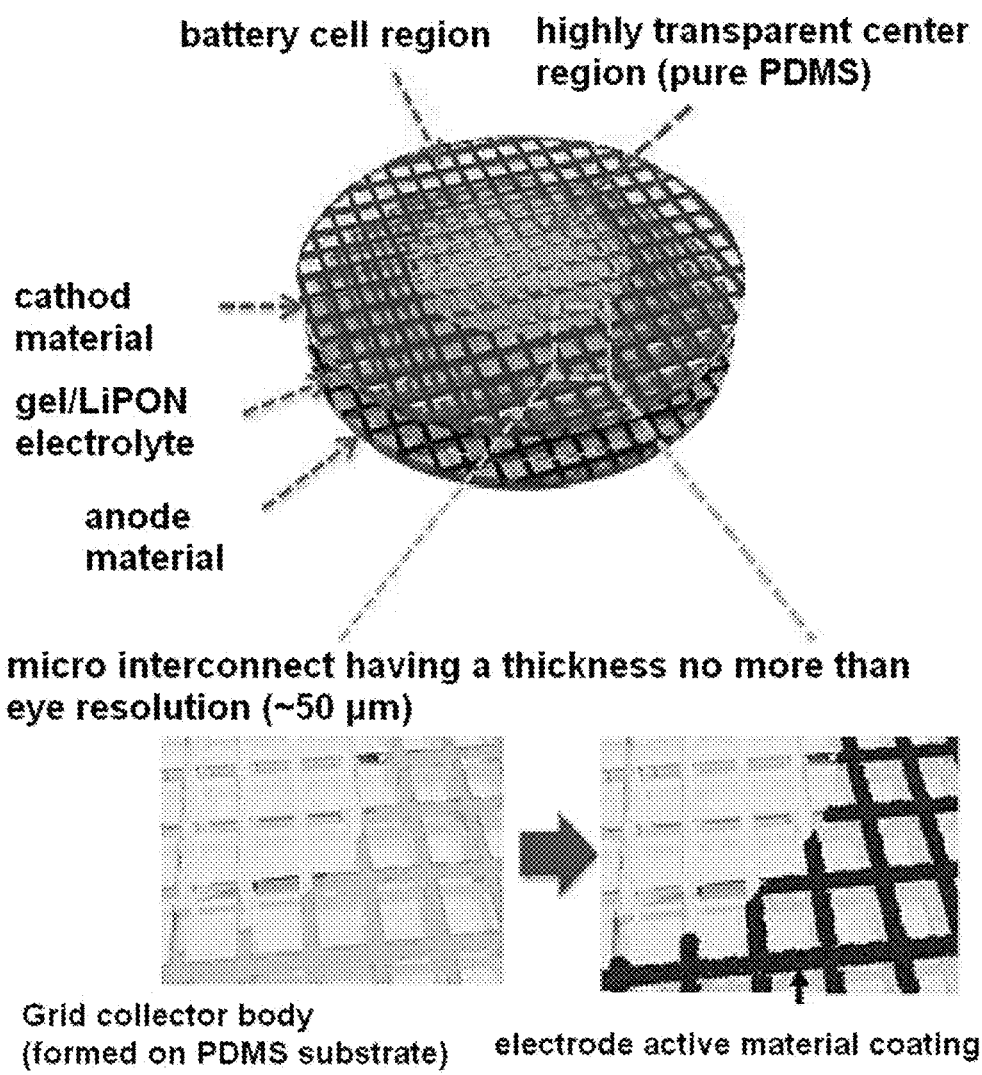
FIG. 7 is a conceptual diagram of mesh type secondary battery.
Figure 8:
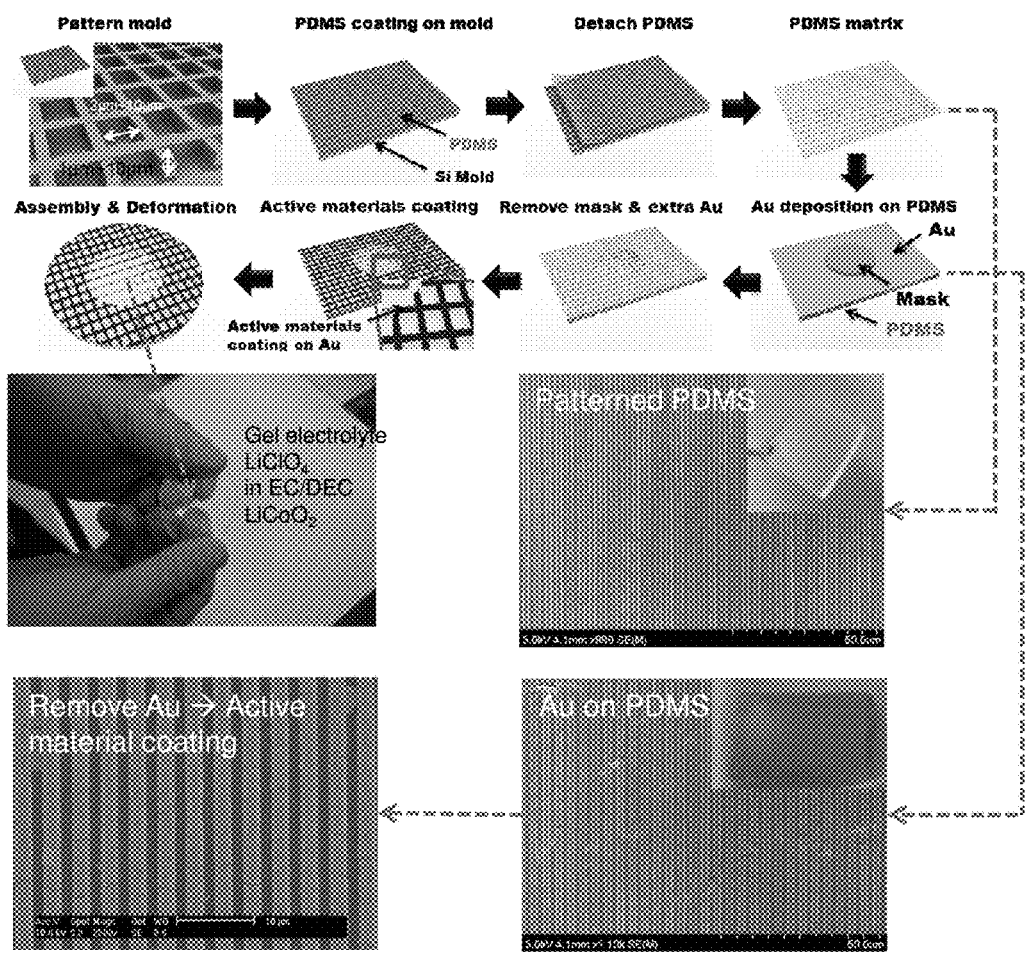
FIG. 8 shows a process drawing of mesh type secondary battery and SEM images of mesh structure obtained from each process step. Inset of each image is a photo of a materialized sample and the photos of final results show samples materializing transparent mesh structure on a flexible substrate.

FIG. 4(b) shows amperometric current response on anonenzymatic gold/platinum nanoparticle electrode, as shown in the example 4, measuring current changes with respect to glucose level change. After 40 ul of gold/platinum nanoparticles was fixed on the CNT functionalized screen printed electrode by drop-casting method, 0.5V of potential was applied to the electrode in 0.1 M PBS, and amount of current generated with 5 mM injection of glucose solution with 100 sec of interval was measured. It was identified that as the glucose amount increased, the generated current accordingly increased. The sensitivity was 18 μA/(mM·cm$^2$).

<Example 5> Electrode Thin Film for a Transparent Battery

A transparent battery has a laminated structure where transparent current collector, anode, solid electrolyte, cathode, and current collector thin film were stacked orderly. As the transparent current collector thin film, a transparent oxide electrode such as ITO, AZO, and GZO were formed through sputtering process, transparent anode thin film such as graphene or Li4Ti5O12 was evaporated on that, and then transparent solid electrolyte such as LiPON was evaporated by sputtering method. The transparent cathode thin film was formed by evaporation of LiMPO4 (M=Fe, Ni) with sputtering method and its detailed contents were as follows.

Figure 9A:
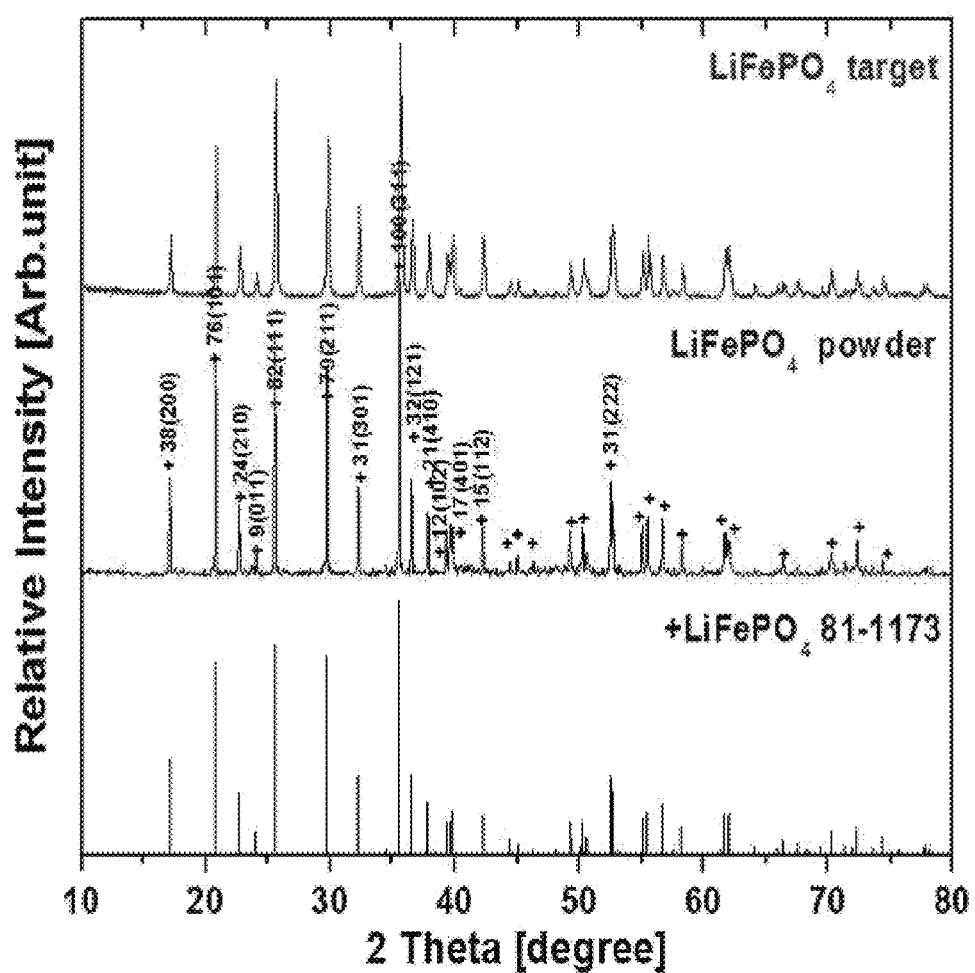
FIG. 9A shows characterization results of power storing device prepared by using LiFePO4, a cathode material of the secondary battery, in complete transparent battery—synthesis results of LiFePO4 determined with X-ray diffraction (XRD).
Figure 9B:
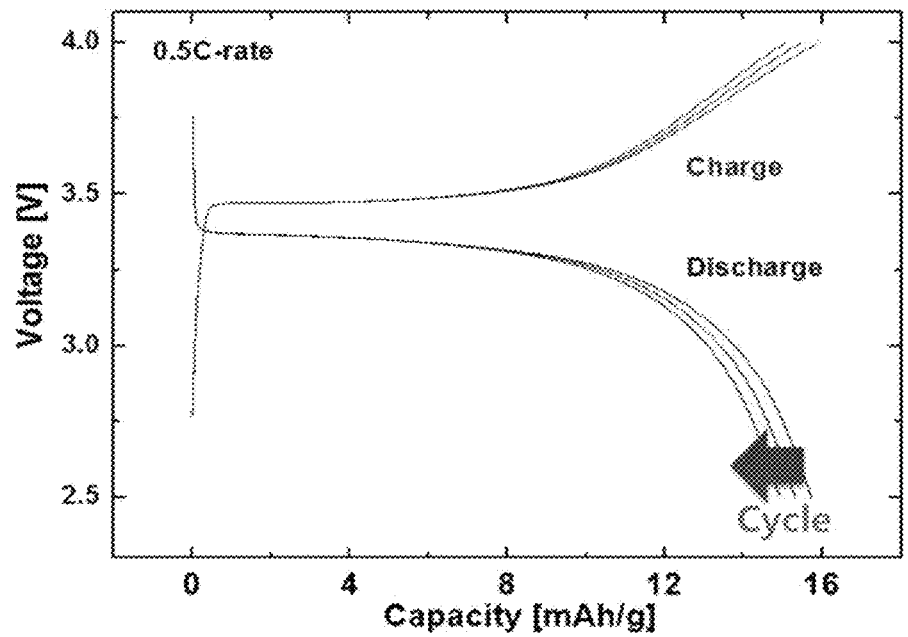
FIG. 9B shows characterization results of power storing device prepared by using LiFePO4, a cathode material of the secondary battery, in complete transparent battery—results of charging and discharging property measurement by preparing the cathode material in the form of a coin cell.
Figure 9C:
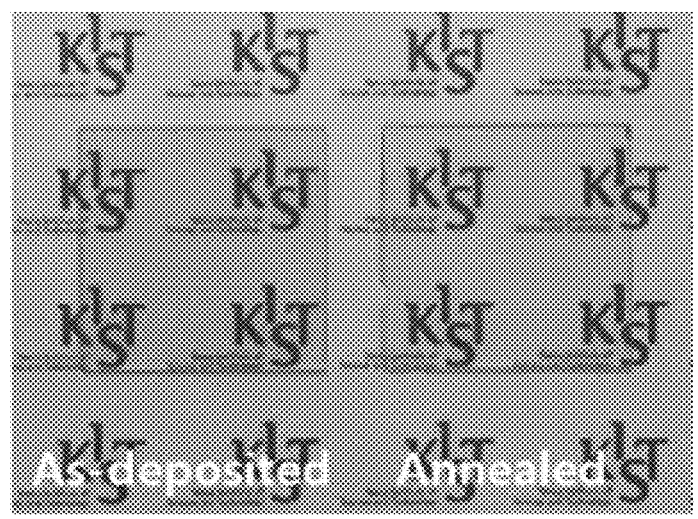
FIG. 9C shows characterization results of power storing device prepared by using LiFePO4, a cathode material of the secondary battery, in complete transparent battery—a photo of a sample with transparency in case of evaporating the cathode material on an organic substrate.
Figure 9D:
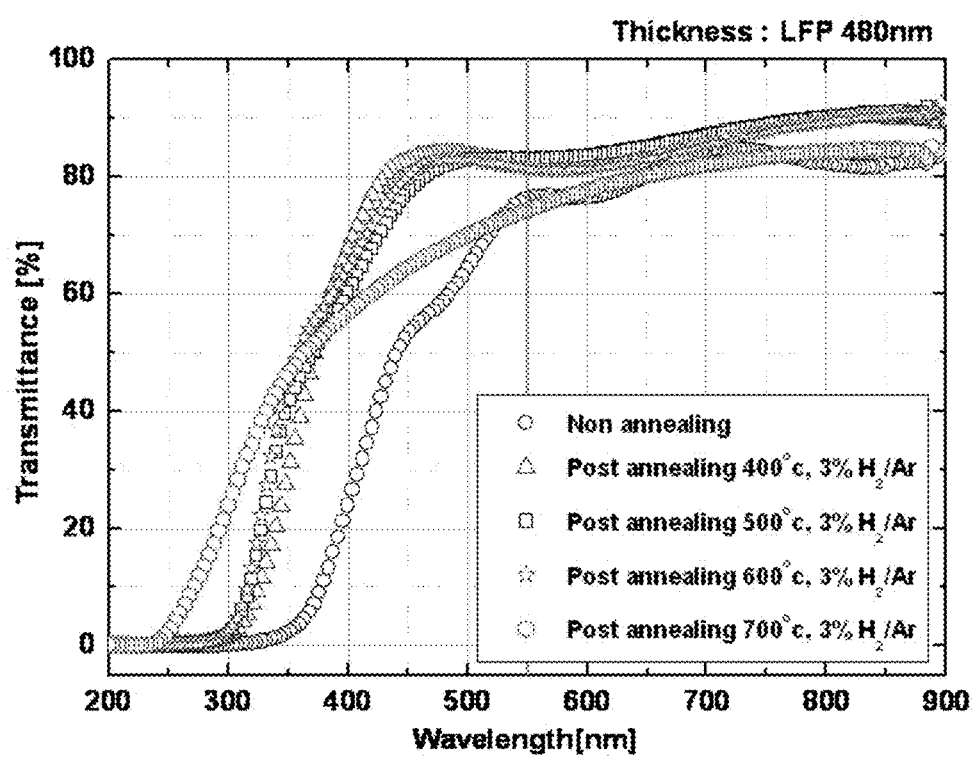
FIG. 9D shows characterization results of power storing device prepared by using LiFePO4, a cathode material of the secondary battery, in complete transparent battery—transparency measurement curve of the transparent thin film.
Figure 10:
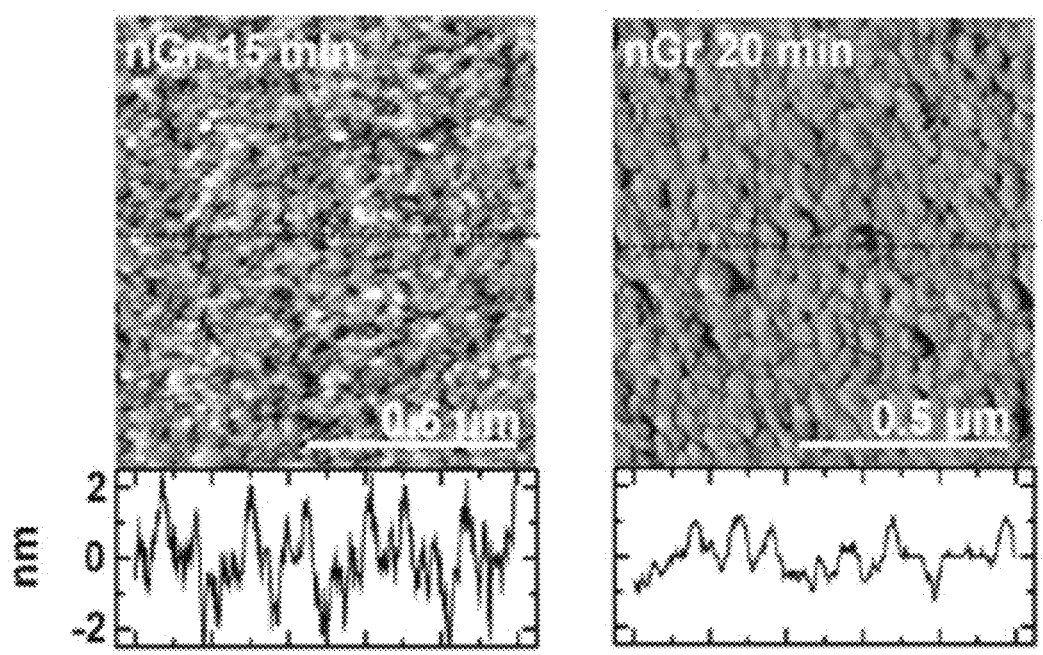
FIG. 10 is Atomic Force Microscope (AFM) images of graphene to be used for an electrode, a collector body or an interconnect in the sensor module and the power storage module and examples of samples whose crystal grain size were controlled differently according to process.

Single-phase target with composition of LiFePO4 was sputtered on a glass substrate with RF magnetron sputtering (Samwon Vacuum, Korea). As the substrate, 1.5 cm×1.5 an sized substrate was used and prepared by washing with acetone for 15 min, methanol for 15 min, and DI water for 15 min using a sonicator, followed by the water removal with $N_2$ gas to clean the substrate before membrane formation. Initial vacuum degree before membrane formation was no more than $5\times10^{-6}$ mTorr and the thin film was prepared under 5 mTorr of pressure during the membrane formation. Output power in the membrane formation step was fixed at 160 W (4" target, 2 W/cm$^2$) drawn as optimal condition through the preliminary experiment. For crystallization of the thin film, the thin film was prepared by fixing the temperature of substrate at the room temperature and thermal treatment was performed under a reducing atmosphere in the atmosphere adjustable furnace, injecting 3% $H_2$/(Ar+$H_2$) in 800 cc/min of rate. At this time, the thermal treatment temperature was 500° C. and thermal treatment was performed with 3° C./min of temperature increase for 2 hr. After thermal treatment in the atmosphere furnace, crystals would be generated. FIG. 9 shows characterization results of secondary battery materialized by using LiFePO4. FIG. 9(a) identified the success of material synthesis using XRD and FIG. 9(b) showed measurement results of charging and discharging characteristics by preparing the synthesized cathode in a form of a coin cell. In addition in FIGS. 9(c) and (d), transparency of the synthesized material was analyzed.

Figure 11A:
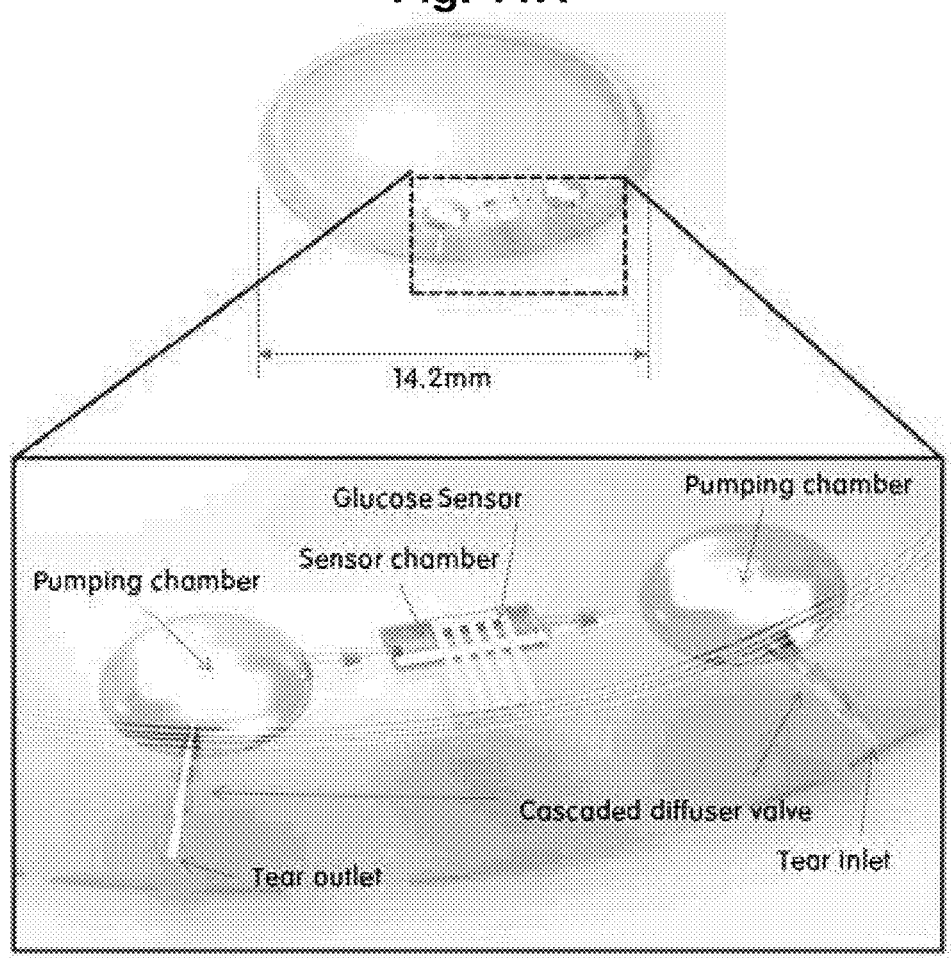
FIG. 11A shows a membrane structure located on the most outer layer of the contact lens, which comprises a pump, valves, and pipes to circulate tear continuously into a chamber in which the sensor part is located.
Figure 11B:
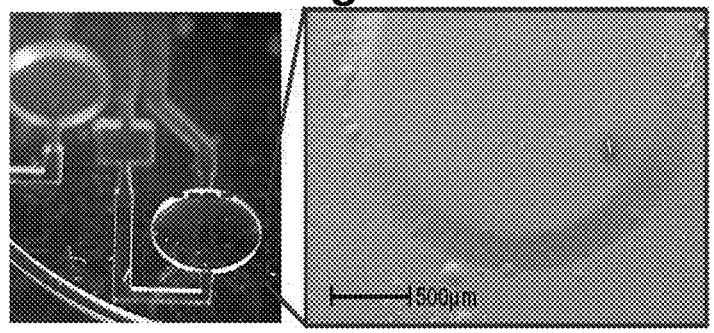
FIG. 11B represents an example of a designed pump and pipe.
Figure 12A:
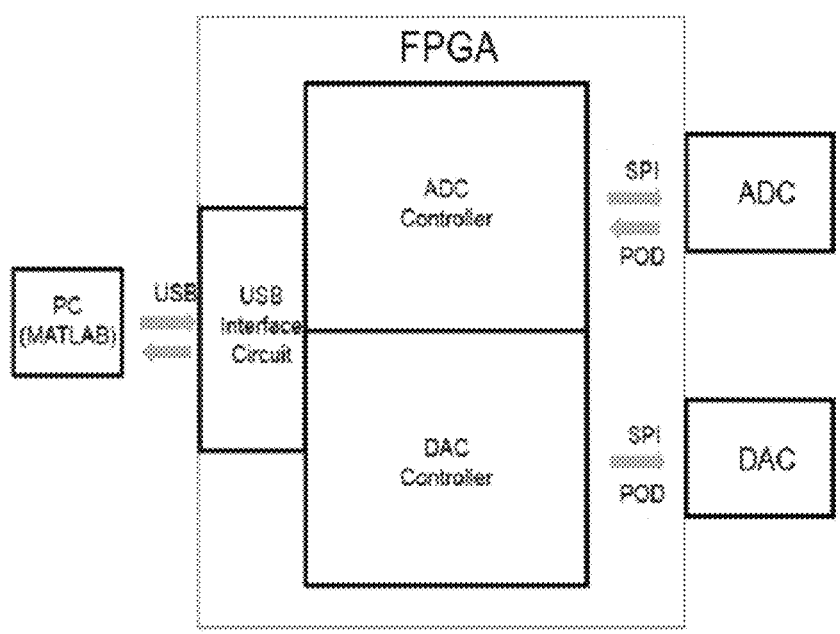
FIG. 12A shows the sensor driving module schematically.
Figure 12B:
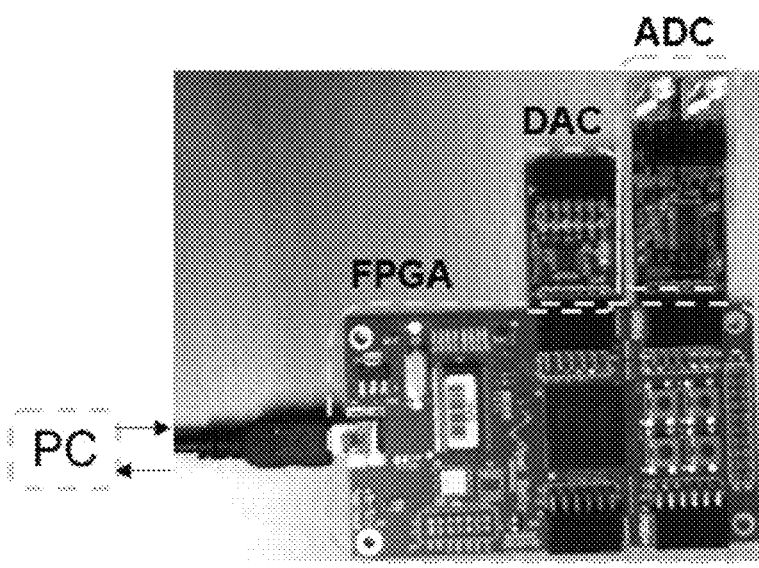
FIG. 12B shows a photo of a materialized module example.
Figure 13A:
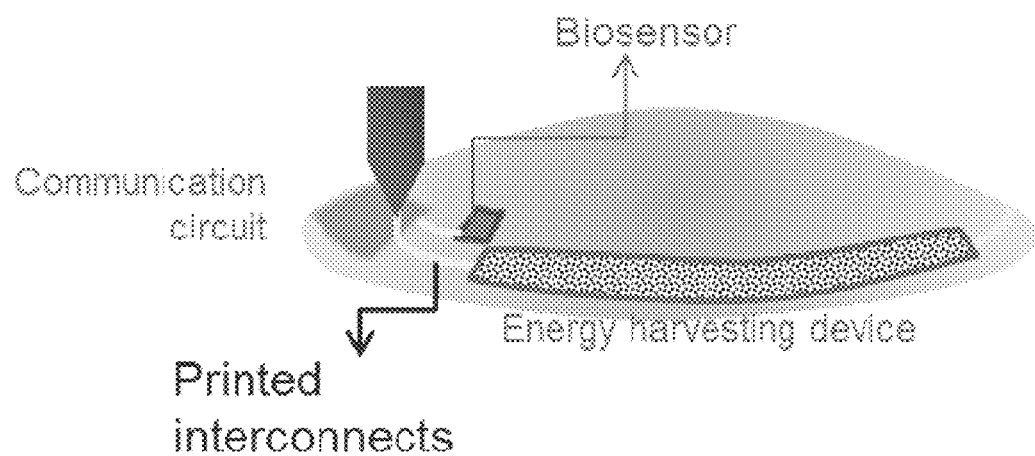
FIG. 13A is an interconnect diagram between functional modules, showing an interconnect materialized with a printing method.
Figure 13B:
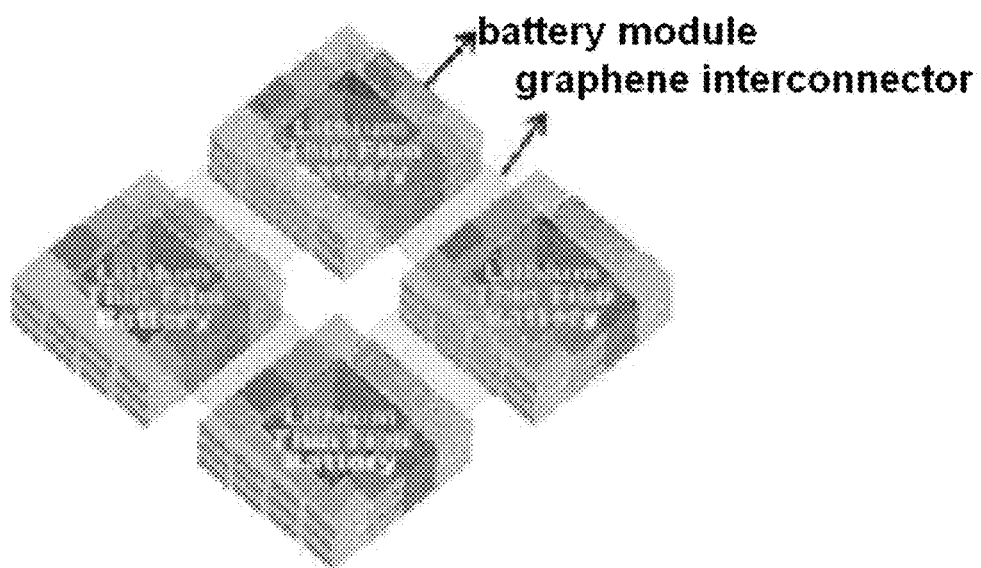
FIG. 13B is a interconnect diagram between functional modules, showing an interconnect materialized with graphene transferring method.

<Example 6> Design and Preparation of the Most Outer Layer of Membrane Structure Comprising Pump, Valve, and Pipe The protective membrane structure located at the most outer layer of the contact lens that provides tear to the sensor device continuously and protects the sensor device from motion and pressure of eyelid was shown in FIG. 11, and FIG. 11(b) is a photo of an example. The protective membrane structure of an example comprises a manual pump to circulate the tear, a diffuser valve to prevent reverse flow of the tear, a sensor chamber where the fluid flowing along the pipe can contact with the sensor device and pipes connecting them. All the structures are arranged within 5 mm of outer rim of the lens not to interfere the view. The structure of example is prepared by bonding 2 thin PDMS (polydimethylsiloxane) or Nusil MED-6015 sheets with 70 µm of thickness and cutting it in a circle shape with 14.2 mm of diameter. A pump chamber, valve, sensor chamber, and a groove with 50 µm of depth following the shape of channel structure are formed at the bottom of the upper side sheet having a contact with the eyelid. Thus, when the upper side sheet is bound with a lower side sheet, a pipe where the tear flows and a chamber where the fluid is accumulated would be formed.

The manual pump is composed of a circular prominent part with 40 µm of thickness, a circular septum with 60 µm of total thickness comprising the prominent part, and a circular tear chamber with 50 µm of height and 1 mm 1.5 mm, or 2 mm of diameter. When blinking the eyelid, the pressure and sheer force of the eyelid passing through in state of pressing the surface of lens presses the prominent part having the septum downward and the lachrymal chamber is pressed to extrude the tear by it. In order to make the tear extruded by the manual pump flow only in one direction, diffuser valves are arranged on both ends of inlet and outlet. The diffuser valve which is a pipe whose width increases gradually has a property that the fluid flow well in a direction of pipe widening, but does not flow well in the contrary direction and the diffuser valve of the example uses 5°~10° of widening angle.

Because the diameter of the pump chamber and the widening angle of diffusor valve influences flow rate of the tear by the manual pump, they are combined properly by calculation and 2 or 4 chambers can be designed to connect parallel to increase flux. The width of pipe where the tear flows is decided according to flux and the width of the example is 200 µm or 300 µm.

As results of test for flux of manual pump for circulation, valve, and pipe structure of the example, it was found that the flux was about 2.5~4 µl/min in 20 times/min of pump operation.

<Example 7> Preparation of Nanoparticle Ink Mixture of Carbon Nano Material and Polydopamine The polydopamine nanoparticle is prepared through below process. Dissolve 15 mg of dopamine in 30 ml of pH 8.5 tris-HCl basic buffer solution using HCl and stir it for 12 hr. The color of solution changes to transparent gray with formation of polydopamine nanoparticle. After separating large precipitated particles from the solution with centrifuge, polydopamine nanoparticle dispersed solution was obtained.

The poly dopamine solution was mixed with carbon nano material dispersed solution in a certain ratio to prepare ink mixture. In this example, multiple wall carbon nanotube and graphene were used as conductive carbon nano material. Add 50 mg of multiple wall carbon nanotube in 10 ml of 0.5 wt % graphene oxide dispersed solution and prepare carbon nanotube dispersed solution by performing sonication for 30 min. The graphene oxide plays a role as a dispersant to disperse the carbon nanotube in water and plays further a role to reduce resistance of the interconnect through later reducing process.

Figure 14:
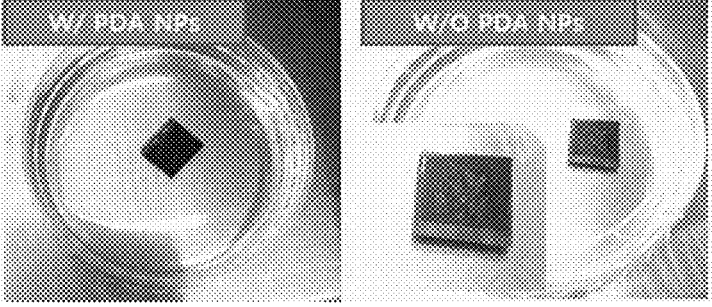
FIG. 14 shows results of ink development for interconnect to be materialized with printing method, which explains electrical properties and substrate adhesiveness of carbon nano material and polydopamine mixed ink by compositions according to existence of polydopamine.
Figure 15:
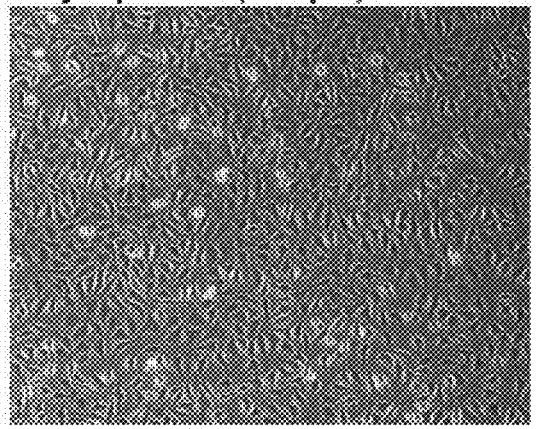
FIG. 15 is a result of toxicity test for carbon nano material and polydopamine mixed ink, which shows that there is no specific toxicity for the used ink.
Figure 16:
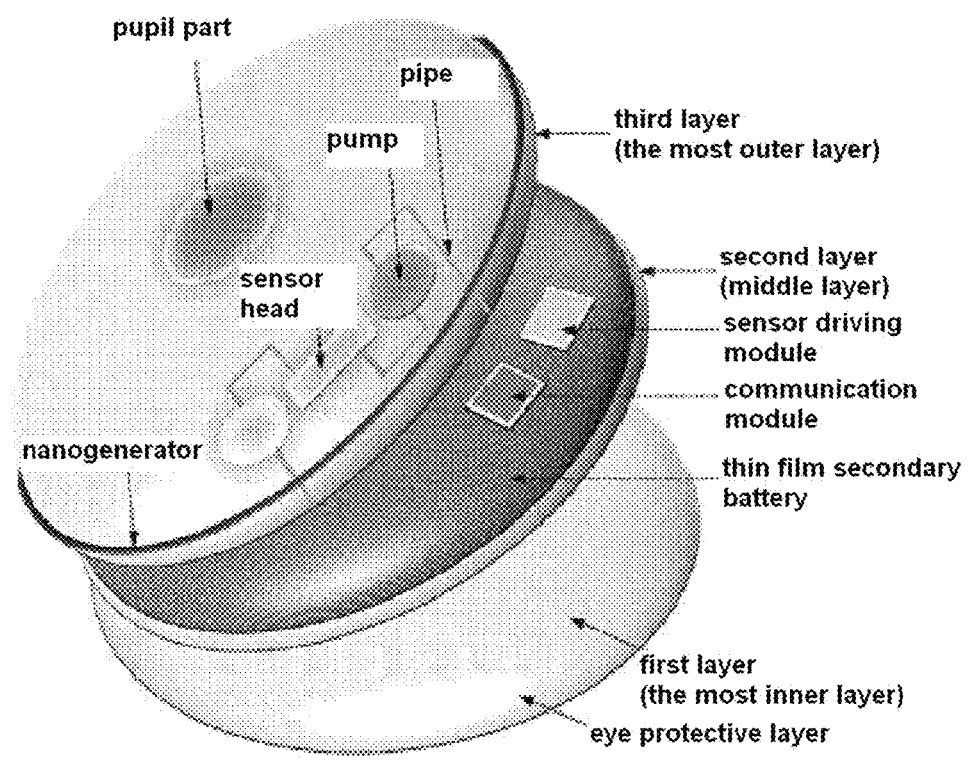
FIG. 16 is a conceptual diagram of contact lens type system, an example of a noninvasive system of the present invention.

Prepare the ink mixture by mixing the prepared carbon nano material solution with polydopamine nanoparticle solution in a certain ratio. After coating or patterning the ink on the substrate, graphene oxide was reduced by using hydrazine reducing agent. The reduction process is not limited in the above method and commonly used light or heat treatment may result in same effect. FIG. 14 shows results of sheet resistance of carbon nano material/polydopamine nanoparticle ink mixture with 4-probe conductivity meter. As results of adhesiveness strength test of carbon nano material/polydopamine nanoparticle ink mixture and carbon nano material ink in solution after leaving them for 1 week, it was identified that as shown in FIG. 15 the adhesiveness property was improved when polydopamine particle was added.

<Example 8> Biocompatibility Test for Biocompatibility Test, US Fad Certified Testing Method for Contact Lens was Applied In biocompatibility test before animal test, L929 cell line (mouse C3H/An connective tissue) cultured with DMEM, penicillin, streptomycin, and fetal bovine serum was used Material substance of device, completed device, and contact lens sample were placed on the surface of agarose where L929 cells were cultured and the number of cells changed to be toxic or lysed among the number of total cells was indicated as ratio to measure bio toxicity degree.

The method known as biocompatibility test is performed by placing liquids such as contact lens dissolved material, saline solution and cleaner onto cell cultured agarose surface, and the degree of the biocompatibility is expressed as a ratio of the number of cells changed to be toxic or lysed over the total number of cells. As the material substance of device and completed device exist in solid form, it was tested if there is toxic material dissolved into the medium with transformation of L929 cells by putting them into the media of L929 cells. This toxicity test was performed for electrode material of sensor and ink materials to be used as interconnect between modules. In FIG. 15, optical microscope image was presented as test result and it was identified that there was no significant toxicity. If any significant toxic material is found, it is planned to perform MTT assay to quantify the cellular response to the concentration of toxic material. MTT assay is a technology to measure cellular enzymatic activity with color change.

As the present features may be embodied in several forms without departing from the characteristics thereof, it should further be understood that the above-described embodiments are not limited by any of the details of the foregoing description, unless otherwise specified, but rather should be construed broadly within its scope as defined in the appended claims, and therefore all changes and modifications that fall within the metes and bounds of the claims, or equivalents of such metes and bounds are therefore intended to be embraced by the appended claims.

What is claimed is:

1. A noninvasive health indicator monitoring system for use in collecting at least one health indicator information, comprising
   a sensing module to collect health indicator information obtained from at least one health indicator marker wherein the sensing module includes an enzymatic amperometric sensor comprising:
   glucose oxidase, and
   horseradish peroxidase (HRP) combined onto an M13 virus in which the combined HRP-M13 virus is bound to a carbon nanotube;
   a power storage module located on a support board to provide electric power to the sensing module continuously; and
   a circuit module connected with the sensing module and the power storage module respectively to drive the sensing module, save or transmit the collected health indicator information, and control power supply of the system.

2. The noninvasive health indicator monitoring system according to claim 1, wherein the circuit module comprises a sensor driving part to drive the sensing module, a data control part to control the health indicator information, a transmission part to deliver the health indicator information to an external device.

3. The noninvasive health indicator monitoring system according to claim 1, further comprising a power generation module which is electrically connected with the power storage module.

4. The noninvasive health indicator monitoring system according to claim 1, wherein the system comprises multi-layer structure comprising a first, a second, and a third layer; the first layer is configured to be in contact with the subject; the second layer is located on the first layer and comprises the power storage module and the circuit module; and the third layer is located on the second layer and comprises the sensing module,
   wherein the multilayer structure is at least partially transparent and generally flexible; has a shape of contact lens; and is located between the eyeball and the eyelid in a driving mode.

5. The noninvasive health indicator monitoring system according to claim 4, wherein the power generation module is on the third layer.

6. The noninvasive health indicator monitoring system according to claim 5,
   wherein the power generation module comprises a triboelectric nanogenerator that comprises one nano structure selected from the group consisting of PDMS, polymeric nanostructure and the combinations thereof.

7. The noninvasive health indicator monitoring system according to claim 4, wherein the health indicator information is blood glucose level and the health indicator marker is tear glucose level.

8. The noninvasive health indicator monitoring system according to claim 4, wherein the health indicator marker is one selected from the group consisting of glucose level, glycated albumin level, fructosamine level, 1,5-anhydroglucitol level, uric acid level, lactic acid level, pyruvate level, and ascorbate level.

9. The noninvasive health indicator monitoring system according to claim 4, wherein the sensing module, the power generation module, the power storage module and the circuit module are connected together though interconnect and the interconnect is biocompatible, flexible and transparent interconnect or micro interconnect having the line width of no more than 50 μm.

10. The noninvasive health indicator monitoring system according to claim 9, wherein the interconnect comprises one selected from the group consisting of conductive nanoparticle, nanosized metal structure, oxide semiconductor, conductive polymer, carbon nanotube, and graphene.

11. The noninvasive health indicator monitoring system according to claim 4, wherein the power storage module comprises a laminated flexible thin film battery.

12. The noninvasive health indicator monitoring system according to claim 11, wherein the laminated flexible thin film battery comprises a transparent cathode material, a transparent electrolyte, and a transparent anode material.

13. The noninvasive health indicator monitoring system according to claim 1,
   wherein the sensing module further comprises a filter to filter proteins and the enzymatic amperometric sensor is configured to quantify the health indicator marker from a body fluid filtered through the filter;
   the circuit module connected with the sensing module obtains the health indicator information and saves and transmits the obtained health indicator information; and
   the sensing module comprises a multi-sensor array.

14. The noninvasive health indicator monitoring system according to claim 4, wherein the system has a thickness of no more than 300 μm; comprises a light transmission part comprising micro interconnect which is transparent; and the light transmission part has a diameter of 0.5~2 mm.

15. The noninvasive health indicator monitoring system according to claim 1,
wherein a carboxylic acid functional group (—COOH) of the horseradish peroxidase (HRP) is combined with an amine group (—NH2) of a protein of the M13 virus using 1-ethyl 1-3-(3-dimethylaminopropyl) carboimide and N-hydroxysulfosuccinimide.

16. The noninvasive health indicator monitoring system according to claim 13, wherein the sensing module further comprises metal nanoparticles selected from the group consisting of Au, Pt and the combination thereof.

17. The noninvasive health indicator monitoring system according to claim 4, wherein the supporting substrate in the multilayer structure comprises a soft hydrogel material, the multilayer structure further comprises a protective layer covering whole of the multilayer structure, and the protective layer further comprises one selected from the group consisting of HEMA, soft hydrogel, silicone acrylate, and fluoro-silicone acrylate.

18. The noninvasive health indicator monitoring system according to claim 1, wherein the power storage module is supplied with energy in wireless charging manner.

19. The noninvasive health indicator monitoring system according to claim 18, wherein the wireless charging manner is magnetic resonance.

20. A contact lens comprising:
a first layer;
a second layer on the first layer, wherein the second layer comprises:
a sensor driving module, and
a circuit module electrically coupled to the sensor driving module; and
a third layer on the second layer, wherein the third layer comprises:
an inlet pumping chamber fluidly coupled to a tear inlet,
a sensor chamber fluidly coupled to the inlet pumping chamber;
an enzymatic amperometric sensor electrically coupled to the sensor driving module and to the circuit module, wherein the enzymatic amperometric sensor comprises:
glucose oxidase, and
horseradish peroxidase (HRP) combined onto an M13 virus in which the combined HRP-M13 virus is bound to a carbon nanotube; and
a outlet pumping chamber fluidly coupled to the sensor chamber and fluidly coupled to a tear outlet.

21. The contact lens of claim 20, wherein the second layer further comprises an energy harvesting device electrically coupled to the circuit module.

22. The contact lens of claim 20, wherein the second layer further comprises a thin film battery electrically coupled to the sensor driving module and electrically coupled to the circuit module.

23. The contact lens of claim 20, wherein the third layer further comprises a power generation module electrically coupled to the sensor driving module, to the circuit module, and to the sensor chamber.

24. The contact lens of claim 20, wherein the contact lens is configured to collect at least one health indicator information when in contact with an eye of a subject.

25. The contact lens of claim 20, wherein the third layer further comprises a power generation module; and the second layer further comprises a power storage module which is electrically coupled to the power generation module, to the enzymatic amperometric sensor, to the sensor driving module, and to the circuit module.

26. The contact lens of claim 20, wherein the first, second, and third layers are at least partially transparent.

27. The contact lens of claim 25, wherein the power generation module is selected from the group consisting of thin film type solar cell, a piezoelectric nanogenerator, and a triboelectric nanogenerator.

28. The contact lens of claim 27 wherein the thin film type solar cell is selected from the group consisting of a quantum dot photoelectronic (QDP) device selected from the group consisting of a SnS QDP device, a CuInSe QDP device, a CuS QDP device, and a FeS QDP device.

29. The contact lens of claim 27 wherein the piezoelectric nanogenerator comprises a nano structure of lead-free piezoelectric nano wire selected from the group consisting of ZnO, NKN, BaTiO3, and combinations thereof.

30. The contact lens of claim 27, wherein the triboelectric nanogenerator comprises one nano structure selected from the group consisting of PDMS, polymeric nanostructure, and the combinations thereof.

31. The contact lens of claim 24, wherein the health indicator information is selected from the group consisting of glucose level, glycated albumin level, fructosamine level, 1,5-anhydroglucitol level, uric acid level, lactic acid level, pyruvate level, ascorbate level, and the combinations thereof.

32. The contact lens of claim 20, wherein the sensing module, the power generation module, the power storage module and the circuit module are connected together though interconnect and the interconnect is biocompatible, flexible and transparent interconnect or micro interconnect having line widths of no more than 50 μm.

33. The contact lens of claim 20, wherein a carboxylic acid functional group (—COOH) of the horseradish peroxidase (HRP) is combined with an amine group (—NH2) of a protein of the M13 virus using 1-ethyl 1-3-(3-dimethylaminopropyl) carboimide and N-hydroxysulfosuccinimide.

34. A contact lens comprising:
an enzymatic amperometric sensor that includes:
glucose oxidase, and
horseradish peroxidase (HRP) combined onto an M13 virus in which the combined HRP-M13 virus is bound to a carbon nanotube;
a sensor driving module electrically coupled to the enzymatic amperometric sensor,
a circuit module electrically coupled to the sensor driving module;
a power storage module electrically coupled to the sensor driving module and to the circuit module;
a tear inlet;
an inlet pumping chamber fluidly coupled to the tear inlet;
a sensor chamber fluidly coupled to the inlet pumping chamber in which the enzymatic amperometric sensor is at least partially contained therein;
outlet pumping chamber fluidly coupled to the sensor chamber; and
a tear outlet fluidly coupled to the outlet pumping chamber.

35. The contact lens of claim 34, wherein a carboxylic acid functional group (—COOH) of the horseradish peroxidase (HRP) is combined with an amine group (—NH2) of a protein of the M13 virus using 1-ethyl 1-3-(3-dimethylaminopropyl) carboimide and N-hydroxysulfosuccinimide.

36. The contact lens of claim 34, further comprising an energy harvesting device electrically coupled to the circuit module.

37. The contact lens of claim 34, further comprising a filter fluidly coupled between the sensor chamber and the tear inlet.

\* \* \* \* \*